(12) United States Patent
Masuda et al.

(10) Patent No.: US 7,576,053 B2
(45) Date of Patent: Aug. 18, 2009

(54) METHODS AND COMPOSITIONS FOR TREATING DEGENERATIVE BONE DISORDERS

(75) Inventors: Esteban Masuda, Menlo Park, CA (US); Polly Pine, Los Altos, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 466 days.

(21) Appl. No.: 11/452,767

(22) Filed: Jun. 13, 2006

(65) Prior Publication Data

US 2007/0004626 A1    Jan. 4, 2007

Related U.S. Application Data

(60) Provisional application No. 60/690,351, filed on Jun. 13, 2005.

(51) Int. Cl.
A61K 38/00 (2006.01)
A61K 31/66 (2006.01)
A61K 31/28 (2006.01)

(52) U.S. Cl. .................. 514/2; 514/102; 514/256; 514/492

(58) Field of Classification Search .............. 514/2, 514/102, 256, 492
See application file for complete search history.

(56) References Cited

U.S. PATENT DOCUMENTS

| | | | |
|---|---|---|---|
| 4,866,048 A | 9/1989 | Calverley et al. |
| 5,194,431 A | 3/1993 | Deluca et al. |
| 5,206,229 A | 4/1993 | Calverley et al. |
| 5,292,728 A | 3/1994 | Neef et al. |
| 5,446,035 A | 8/1995 | Neef et al. |
| 5,532,228 A | 7/1996 | Neef et al. |
| 6,242,434 B1 | 6/2001 | Bishop et al. |
| 6,284,730 B1 | 9/2001 | Dietrich et al. |
| 6,534,524 B1 | 3/2003 | Kania et al. |
| 6,573,295 B2 | 6/2003 | Shakespeare et al. |
| 6,762,179 B2 | 7/2004 | Cochran et al. |
| 6,835,722 B1 | 12/2004 | Kang et al. |
| 6,849,641 B1 | 2/2005 | Tang et al. |
| 6,897,207 B2 | 5/2005 | Cox et al. |
| 6,897,208 B2 | 5/2005 | Edwards et al. |
| 7,060,827 B2 | 6/2006 | Singh et al. |
| 7,122,542 B2 | 10/2006 | Singh et al. |
| 7,329,671 B2 | 2/2008 | Singh et al. |
| 7,329,672 B2 | 2/2008 | Singh et al. |
| 7,332,484 B2 | 2/2008 | Singh et al. |
| 2004/0029902 A1 | 2/2004 | Singh et al. |
| 2004/0106615 A1 | 6/2004 | Cochran et al. |
| 2004/0142947 A1 | 7/2004 | Cox et al. |
| 2004/0198750 A1 | 10/2004 | Green et al. |
| 2004/0214817 A1 | 10/2004 | Pierce et al. |
| 2005/0004152 A1 | 1/2005 | Cochran et al. |
| 2005/0009876 A1 | 1/2005 | Bhagwat et al. |
| 2005/0113398 A1 | 5/2005 | Argede et al. |
| 2005/0209230 A1 | 9/2005 | Singh et al. |
| 2005/0234049 A1 | 10/2005 | Singh et al. |
| 2006/0035891 A1 | 2/2006 | Li et al. |
| 2006/0058525 A1 | 3/2006 | Singh et al. |
| 2006/0135543 A1 | 6/2006 | Singh et al. |
| 2006/0167254 A1 | 7/2006 | Cooper et al. |
| 2006/0211657 A1 | 9/2006 | Singh et al. |
| 2006/0234983 A1 | 10/2006 | Singh et al. |
| 2006/0270694 A1 | 11/2006 | Wong |
| 2006/0293311 A1 | 12/2006 | Li et al. |
| 2007/0060603 A1 | 3/2007 | Singh et al. |
| 2007/0117775 A1 | 5/2007 | Payan |
| 2007/0167439 A1 | 7/2007 | Singh et al. |
| 2007/0197782 A1 | 8/2007 | Clough et al. |
| 2007/0203161 A1 | 8/2007 | Argade et al. |
| 2007/0203162 A1 | 8/2007 | Li et al. |
| 2007/0225321 A1 | 9/2007 | Singh et al. |
| 2007/0225495 A1 | 9/2007 | Singh et al. |
| 2007/0293520 A1 | 12/2007 | Singh et al. |
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299095 A1 | 12/2007 | Singh et al. |

FOREIGN PATENT DOCUMENTS

| | | |
|---|---|---|
| WO | WO 99/47529 | 9/1999 |
| WO | WO 00/27802 | 5/2000 |
| WO | WO 02/096905 | 12/2002 |
| WO | WO 03/000688 | 1/2003 |
| WO | WO 03/000695 | 1/2003 |
| WO | WO 03/020698 | 3/2003 |

(Continued)

OTHER PUBLICATIONS

PCT International Search Report from PCT/US2006/023070 dated Dec. 12, 2006.
U.S. Appl. No. 11/539,074, filed Oct. 5, 2006, Singh et al.
U.S. Appl. No. 11/539,142, filed Oct. 5, 2006, Singh et al.
U.S. Appl. No. 11/782,581, filed Jul. 24, 2007, Singh et al.
U.S. Appl. No. 11/875,772, filed Oct. 19, 2007, Li et al.
U.S. Appl. No. 11/943,506, filed Nov. 20, 2007, Bhamidipati et al.
U.S. Appl. No. 12/028,581, filed Feb. 8, 2008, Argade et al.
U.S. Appl. No. 12/030,031, filed Feb. 12, 2008, Li et al.

(Continued)

Primary Examiner—Raymond J Henley, III
(74) Attorney, Agent, or Firm—McDonnell Boehnen Hulbert & Berghoff LLP

(57) ABSTRACT

The present disclosure provides methods and compositions using Syk inhibitory compounds for treating degenerative bone disorders and as prophylactic treatment to prevent bone loss. These treatments may reduce the fracture risk associated with bone loss and compromised bone strength.

31 Claims, 4 Drawing Sheets

FOREIGN PATENT DOCUMENTS

Figure 1:
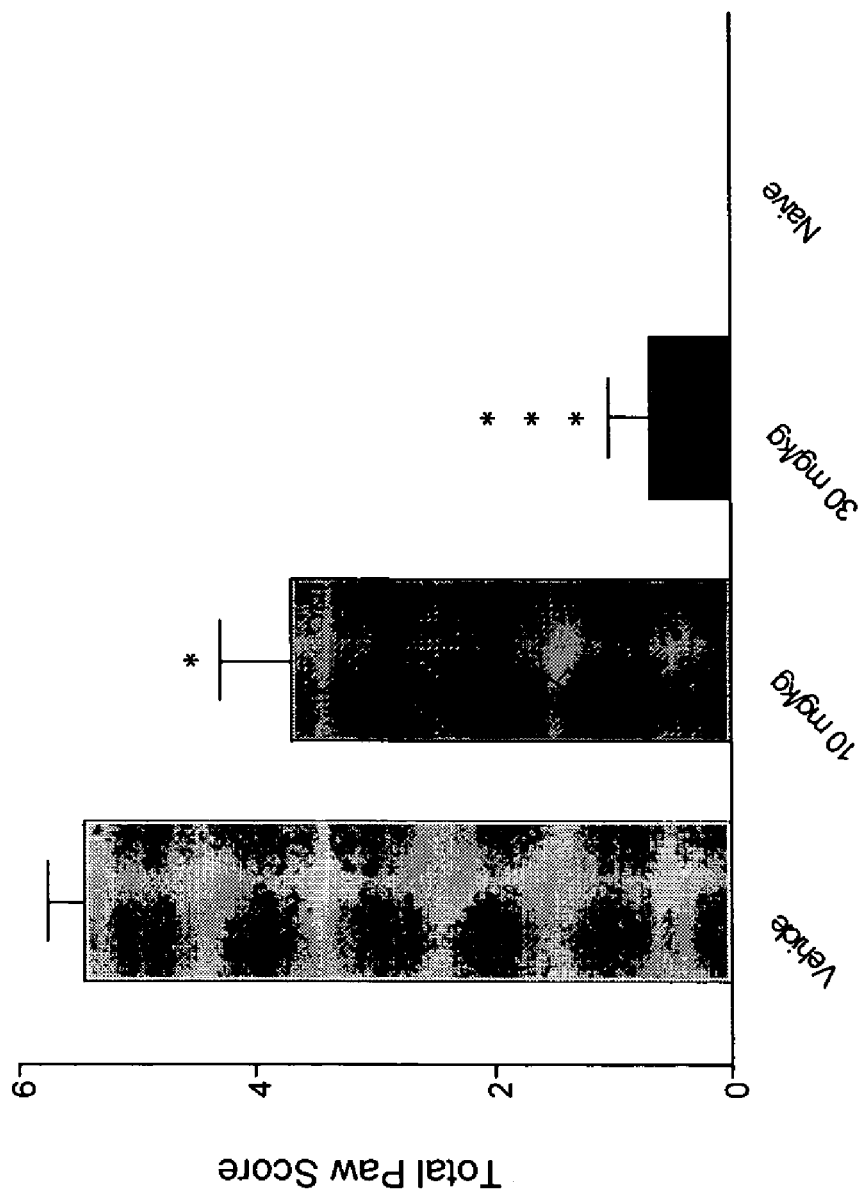

| WO | WO 2004/014382 | 2/2004 |
| --- | --- | --- |
| WO | WO 2004/016597 | 2/2004 |
| WO | WO 2004/046120 | 6/2004 |
| WO | WO 2004/085388 | 10/2004 |
| WO | WO 2004/092154 | 10/2004 |
| WO | WO 2005/013982 | 2/2005 |
| WO | WO 2005/027848 A2 | 3/2005 |
| WO | WO 2006/078846 | 7/2006 |

OTHER PUBLICATIONS

U.S. Appl. No. 12/030,069, filed Feb. 12, 2008, Argade et al.
U.S. Appl. No. 12/053,382, filed Mar. 21, 2008, Atuegbu et al.
U.S. Appl. No. 12/053,438, filed Mar. 21, 2008, Li et al.
U.S. Appl. No. 12/175,441, filed Jun. 17, 2008, Singh et al.
Atkins et al. 2003, "Rankl expression is related to the differentiation state of human osteoblasts" *J. Bone Miner, Res.* 18(6):1088-1098.
Boutry et al. 2003, "Trabecular bone structure of the calcaneus: preliminary in vivo MR imaging assessment in men with osteoporsis" *Radiology* 227(3):708-717.
Clemens et al. 1997, "Evidence that serum NTx (collagen-type I N-telopeptides) can act as an immunochemical marker of bone resorption" *Clin. Chem.* 43(11):2058-2063.
Corral et al. 1998, "Dissociation between bone resorption and bone formation in osteopenic transgenic mice" *Proc. Natl. Acad. Sci. USA* 95(23):13835-13840.
Dempster et al. 2001 "Effects of daily treatment with parathyroid hormone on bone microarchitecture and turnover in patients with osteoporosis: a paired biopsy study" *J. Bone Miner. Res.* 16(10):1846-1853.
Denoto et al. 1981, "Human growth hormone DNA sequence and mRNA structure: possible alternative splicing" *Nucleic Acids Res.* 9(15):3719-3730.
Fox et al. 1998, "A single amino acid substitution makes ERK2 susceptible to pyridinyl imidazole inhibitors of p38 MAP kinase" *Protein Science* 7(11):2249-2255.
Garnero et al. 2001, "Evaluation of a fully automated serum assay for C-terminal cross-linking telopeptide of type I collagen in osteoporosis" *Clin. Chem.* 47(4):694-702.
Ghiron et al. 1995, "Effects of recombinant insulin-like growth factor-I and growth hormone on bone turnover in elderly women" *J. Bone Miner. Res.* 10(12):1844-1852.
Halleen et al. 1999, "Intracellular fragmentation of bone resorption products by reactive oxygen species generated by osteoclastic tartrate-resistant acid phosphatase" *J. Biol. Chem.* 274(33):22907-22910.
Halleen et al. 2001, "Serum tartrate-resistant acid phosphatase 5b is a specific and sensitive marker of bone resorption" *Clin. Chem.* 47(3):597:-600.
Henrotin et al. 2001, "Strontium ranelate increases cartilage matrix formation" *J. Bone Miner. Res.* 16(2):299-308.
Hill et al. 1989, "The preparation of monoclonal antibodies which react preferentially with human bone alkaline phosphatase and not liver alkaline phosphatase" *Clin. Chim. Acata* 186(2):315-320.
Janckila et al. 2003, "Disease-specific expression of tartrate-resistant acid phosphatase isoforms" *J. Bone Miner. Res.* 18(10):1916-1919.
Jiang et al. 2000, "Micro CT and Micro MR imaging of 3D architecture of animal skeleton" *J. Musculoskelet. Neuronal. Interact.* 1(1):45-51.
Jiang et al. 2003, "Recombinant human parathyroid hormone (1-34) [teriparatide] improves both cortical and cancellous bone structure" *J. Bone Miner. Res.* 18(11):1932-1941.
Jilka et al. 1996, "Linkage of decreased bone mass with impaired osteoblastogenesis in murine model of accelerated senescence" *J. Clin. Invest.* 97(7):1732-1740.
Katznelson et al. 1996, "Increase in bone density and lean body mass during testosterone administration in men with acquired hypogonadism" *J. Clin. Endocrin. Metab.* 81(12):4358-4365.
Kawakami et al. 2003, "A Ras activation pathway dependent on Sky phosphorylation of protein kinase C" *Proc. Natl. Acad. Sci. USA* 100(16):9470-9475.

Lai et al. 2003, "Potent small molecule inhibitors of spleen tyrosine kinase (Syk)" *Bioorg. Med. Chem. Lett.* 13(18):3111-3114.
Lau et al. 2003, "Osteoblastic tartrate-resistant acid phosphatase: its potential role in the molecular mechanism of osteogenic action of fluoride" *J. Bone Miner Res.* 18(10):1897-1900.
Lin et al. 1998, "Heterogeneity of trabecular bone structure in the calcaneus using magnetic resonance imaging" *Osteoporos Int.* 8:16-24.
Lubec et al. 1996, "Evidence for McKusick's hypothesis of deficient collagen cross-linking in patients with homocystinuria" *Biochim. Biophys. Acta* 1315(3):159-162.
MacInnis et al. 2003, "Determinants of bone density in 30- to 65-year-old women: a co-twin study" *J. Bone Miner. Res.* 18(9):1650-1656.
Maruyama et al. 1996, "Physical and functional association of cortactin with Syk in human leukemic cell line K562" *J. Biol. Chem.* 271(12):6631-6635.
Mawatari et al. 2000, "Effect of vitamin K2 on three-dimensional trabecular microarchitecture in ovariectomized rats" *J. Bone Miner. Res.* 15(9):1810-1817.
Meunier et al. 2002, "Strontium ranelate: dose-dependent effects in established postmenopausal vertebral osteoporis—a 2-year randomized placebo controlled trial" *J. Clin. Endocrinol. Metab.* 87(5):2060-2066.
Mizuno et al. 2002, "Transgenic mice overexpressing soluble osteoclast differentiation factor (sODF) exhibit severe osteoporosis" *J. Bone Miner. Metab.* 20(6):337-344.
Nakasato et al. 1999, "Clincial significance of immunoassays for type-5 tartrate-resistant acid phosphatase" *Clin. Chem.* 45(12):2150-2157.
National Institutes of Health 1994, "NIH Consensus Statement; Optimal Calcium Intake" Jun. 6-8 12(4):1-30.
Neer et al. 2001, "Effect of parathyroid hormone (1-34) on fractures and bone mineral density in postmenopausal women with osteoporosis" *N. Engl. J. Med.* 344(19): 1434-1441.
Nomiyama et al. 2005, "Identification of genes differentially expressed in osteoclast-like cells" *J. Interferon. Cytokine. Res.* 25(4):227-231.
Pak et al. 1995, "Treatment of postmenopausal osteoporosis with slow-release sodium fluoride. Final report of a randomized controlled trial" *Ann. Inter. Meg.* 123(6):401-408.
Pak et al. 1996, "Slow-release sodium fluoride in osteoporosis" *J. Bone Miner. Res.* 5:561-564.
Peters et al. 1996, "Syk, activated by cross-linking the B-cell antigen receptor, localizes to the cytosol where it interacts with and phosphorylates alpha-tubulin on tyrosine" *J. Biol. Chem.* 271(9):4755-7462.
Petersen et al. 2000, "Identification of osteoblast/osteocyte factor 45 (OF45), a bone-specific cDNA encoding an RGD-containing protein that is highly expressed in osteoblasts and osteocytes", *J. Biol. Chem.* 275(46):36172-36180.
Reginster 2002, "Strontium ranelate in osteoporosis" *Curr. Pharm. Des.* 8(21):1907-1916.
Ringe et al. 1999, "Therapy of established postmenopausal osteoporosis with monofluorophosphate plus calcium: dose-related effects on bone density and fracture rate" *Osteop. Int.* 9(2):171-178.
Robins et al. 1994, "Direct, enzyme-linked immunoassay for urinary deoxypyridinoline as a specific marker for measuring bone resorption" *J. Bone Miner. Res.* 9(10):1643-1649.
Rosen and Bilezikian 2001, "Clinical review 123: Anabolic therapy for osteoporosis" *J. Clin. Endocrinol. Metab.* 86(3):957-964.
Rosenquist et al. 1998, "Serum CrossLaps One Step ELISA. First application of monoclonal antibodies for measurement in serum of bone-related degradation products from C-terminal telopeptides of type I collagen" *Clin. Chem.* 44(11):2281-2289.
Roskam et al. 1979, "Molecular cloning and nucleotide sequence of the human growth hormone structural gene" *Nucleic Acids Res.* 7(2):305-320.
Rowe 2004, "The wrickkened pathways of FGF23, MEPE and PHEX" *Crit. Rev. Oral Biol. Med.* 15(5):264-281.
Ruzzene et al. 1996, "SH2 domains mediate the sequential phosphorylation of HS1 protein by p72syk and Src-related protein tyrosine kinases" *Biochemistry* 35(16):5327-5332.

Sada et al. 2001, "Structure and function of Syk protein-tyrosine kinase" *J. Biochem.* (Tokyo) 130(2):177-186.

Sewon et al. 2004, "Salivary calcium reflects skeletal bone density of heavy smokers" *Arch. Oral Biol.* 49(5):355-358.

Seyedin et al. 1993, "Immunoassay for urinary pyridinoline: the new marker of bone resorption" *J. Bone Miner. Res.* 8(5):635-641.

Shiotani et al. 2002, "Regulation of osteoclast differentiation and function by receptor activator of NFkB ligand and osteoprotegerin" *Anat. Rec.* 268(2):137-146.

Shiraki et al. 2000, "Vitamin K2 (menatetrenone) effectively prevents fractures and sustains lumbar bone mineral density in osteoporosis" *J. Bone Miner. Res.* 15(3):515521.

Spangler et al. 2001, "Smokeless tobacco and osteoporosis: a new relationship?" *Med. Hypotheses* 56(5):553-557.

Takahashi et al. 2002, "S 12911-2 inhibits osteoclastic bone resorption in vitro" *J. Bone Miner. Res.* 18(6):1082-1087.

Tamura et al. 1993, "New resorption assay with mouse osteoclast-like multinucleated cells formed in vitro" *J. Bone Miner. Res.* 8(8):953-960.

Todd et al. 2003, "Osteoporosis and exercise" *Postgrad. Med. J.* 79(932):320-323.

Turner et al. 2000, "Tyrosine kinase SYK: essential functions for immunoreceptor signalling" *Immunology Today* 21(3):148-154.

Wang et al. 1999, "G(s)alpha repression of adipogenesis via Syk" *J. Biol. Chem.* 274(45):32159-32166.

Weinstein et al. 1997, "The effects of androgen deficiency on murine bone remodeling and bone mineral density are mediated via cells of the osteoblastic lineage" *Endocrinology* 138(9):4013-4021.

Weinstein et al. 1998, "Inhibition of osteoblastogenesis and promotion of apoptosis of osteoblasts and osteocytes by glucocorticoids. Potential mechanisms of their deleterious effects on bone" *J. Clin. Invest.* 102(2):274-282.

Wong et al. 2004, "Targeting Syk as a treatment for allergic and autoimmune disorders" *Expert Opin. Investig. Drugs* 13(7):743-762.

METHODS AND COMPOSITIONS FOR TREATING DEGENERATIVE BONE DISORDERS

1. CROSS REFERENCE TO RELATED APPLICATIONS

This application claims benefit under 35 U.S.C. § 119(e) to application Ser. No. 60/690,351, filed Jun. 13, 2005, the contents of which are incorporated herein by reference.

2. TECHNICAL FIELD

The present disclosure relates to methods and compositions for treating degenerative bone disorders and for preventing bone loss.

3. BACKGROUND

Bone is a dynamic organ that turns over continually through bone resorption and bone deposition. This remodeling process functions to maintain calcium balance, repair bone damaged from mechanical stresses, adjust for changes in mechanical load, and remove old bone material that has degraded with age. Bone mass is regulated by a delicate balance between bone resorption mediated by osteoclasts and bone formation mediated by osteoblasts.

Osteoblasts are cells of mesenchymal origin and synthesize the precursors that form the organic extracellular matrix, also called the osteoid or ground substance, which are composed mainly of type I collagen and various non-collagen proteins such as osteocalcin, osteopontin, osteonectin, proteoglycans, and alkaline phosphatases. Once a layer of organic matrix is laid down by the osteoblasts, mineralization occurs through deposition of hydroxyapatite along and within the organic matrix. Osteocalcin, a protein produced by the osteoblasts, binds and concentrates the calcium in the matrix. Consecutive layers of organic matrix added by the osteoblasts through cycles of osteoid secretion and mineralization (appositional growth) form sheets or rings of mineralized matrix, which fuse together to form a lattice structure of connected bone. A proportion of osteoblasts becomes trapped as osteocytes in the lacunae, which is connected by a system of canaliculi. In some conditions, such as in the fetus and certain bone disorders, the organic matrix is arranged in a weave-like form and results in a type of bone referred to as woven, immature, or primitive bone. Changes to stiffness of bone occurs by modulating the level of hydroxyapatite in the matrix, with higher mineral content providing stiffness and rigidity and a lower mineral content providing bone flexibility.

Osteoclasts, the primary cells responsible for bone resorption, arise from hematopoietic cells of the macrophage/monocyte lineage and are multinucleated cells (i.e., polykaryons) that form by fusion of monocytes. Osteoclasts secrete various enzymes that act in dissolution of bone material. For example, tartrate resistant acid phosphatase (TRACP) decalcifies the bone while cathepsin K digests the bone matrix proteins. Osteoclasts also acidify the surrounding environment through vacuolar $H^+$-ATPase activity, thereby further promoting bone disruption.

The development and function of osteoclasts are tightly coupled to the activity of osteoblasts, which secrete cellular factors affecting osteoclast differentiation and activity. The osteoblast protein RANKL (receptor for activating NFkB ligand) is a key regulator that stimulates differentiation of osteoclast precursor cells and activates mature osteoclasts. Osteoblasts also produce a decoy ligand, osteoprotegrin (OPG), which competes with RANKL and inhibits its activity. Expression of RANKL is regulated by cytokines (e.g., IL-1, IL-6, IL-11 and TNF-α), glucocorticoids, and parathyroid hormone (PTH). The presence of RANKL upregulators leads to enhanced bone resorption and a corresponding loss of bone mass. OPG production is upregulated by cytokines IL-1 and TNF-α, steroid hormone β-estradiol, and mechanical stress, thereby stimulating bone formation. In contrast, gluocorticoids, PTH, and prostaglandins suppress production of OPG and thus enhance bone resorption. This intricate interaction between the osteoblasts and osteoclasts provides a mechanism for adapting to conditions requiring additional bone mass (e.g., increased mechanical load) as well as maintenance of bone mass.

The abnormal regulation of osteoclast and osteoblast activities can lead to various degenerative bone disorders. The clinical presentations of these conditions include loss of bone mass and/or decrease in structural integrity of the bone matrix. Both conditions can lead to an increased risk of bone fractures. The most common form of bone degeneration, primary osteoporosis, is a significant health problem because nearly 5 to 20% of the human female population suffers from the condition. Although not as prevalent as in the female population, age-related osteoporosis also affects a significant percentage of males.

Current treatments for degenerative bone disorders include antiresorptive agents such as bisphosphonates, calcitonin, estrogen, and vitamin D supplementation, which limit bone resorption and prevent loss of bone mass. Anabolic agents that promote bone formation have also been studied, with PTH peptide teriparatide and strontium renelate showing promise in restoring or increasing bone mass to levels sufficient to reduce fracture risk. Some of the therapies, such as estrogen, have undesirable side effects while the effectiveness of others, such as vitamin D supplementation, are of questionable application to those already suffering from bone degeneration. Thus, it is desirable to find alternative therapies applicable as independent treatments or useful in combination with other therapeutic agents to treat degenerative bone disorders and as preventatives against bone loss. Moreover, therapies specifically directed against the cellular basis of bone metabolism and remodeling may avoid some of the undesirable side effects associated with some current therapeutic treatments.

4. SUMMARY

The present disclosure provides methods for treating degenerative bone disorders using Syk kinase inhibitors. Generally, the methods comprise administering to a subject afflicted with a bone degenerative disorder an amount of a Syk inhibitory compound effective to treat the disorder. The inhibitor compounds can reduce bone loss and/or increase bone mineral density to reduce fracture risk in the afflicted subject. Bone degenerative disorders that can be treated with the Syk inhibitory compounds include, among others, various forms of osteoporosis (e.g., postmenopausal osteoporosis, senile osteoporosis, juvenile osteoporosis), osteodystrophy, and osteopenia.

Other degenerative bone disorders that can be treated with the Syk inhibitors include those associated with abnormal secretion of a hormone (i.e., endocrinopathy) that affects bone metabolism. Exemplary hormones influencing bone metabolism include androgens (e.g., testosterone), estrogen, parathyroid hormone, calcitriol, and calcitonin. Endocrinopathies that result in bone degeneration include, among others, hypercorticolism, hypogandism, hyperparathyroidism, and hypoparathyroidism.

In some embodiments, the Syk inhibitory compounds can be used to treat bone degenerative disorders associated with a genetic abnormality. The genetic abnormality may affect osteoclast activity, osteoblast activity, or a combination of osteoclast and osteoblast function such that there is an imbalance of bone resorption over bone formation. In some genetic abnormalities, there is excessive bone remodeling that produces a structurally compromised bone structure, resulting in an increased probability of fracture. Syk inhibitory compounds can be used to attenuate the increased bone resorption present in many of these disorders, and where appropriate, increase bone mass sufficiently to decrease the fracture risk. Exemplary genetic disorders characterized by bone degeneration include osteogenesis imperfecta, homocystinuria, gonadal dysgenesis, and hypophosphatasia.

In other aspects, the Syk inhibitory compounds can be used as prophylaxis for reducing or preventing bone loss and thereby reduce the risk of fractures. The inhibitory compounds can be administered to subjects having a risk factor associated with bone loss. These factors may be gender (e.g., females) or age-related. Other risk factors are associated with low calcium intake in the diet, tobacco use, sedentary lifestyle, family history, and genetic background.

Various Syk inhibitors having selectivity for inhibiting Syk kinase activity can be used for the purposes herein. In some embodiments, the Syk inhibitors suitable for the treatments are 2,4-pyrimidinediamine compounds and various derivatives thereof. These include, where applicable, the salts, hydrates, solvates, and N-oxides of the corresponding 2,4-pyrimidinediamine. In some embodiments, the 2,4-pyrimidinediamine compounds can be in the form of prodrugs, including, among others, 2,4-pyrimidinediamines in which one or more of the available primary or secondary amine groups is masked with a progroup. Other Syk inhibitors that can be used include, among others, triazole, azaindole, pyrrolopyrimidine, and indazole based Syk inhibitors.

The Syk inhibitory compounds can be used alone or in combination with bone modulating agents that reduce the level of bone loss (i.e., antiresorptive) or increase bone formation (i.e., osteo-anabolic). Antiresorptive agents attenuate or inhibit bone resorption and include agents such as 1,25 dihydroxyvitamin D3, bisphosphonates, calcitonin, and estrogen. Osteo-anabolic agents promote bone formation and include agents such as parathyroid hormone, parathyroid hormone analogs, androgens, fluoride, strontium, vitamin K2, and growth hormone. The bone modulating agents can be administered adjunctively as a composition, or administered separately or sequentially in combination with the Syk inhibitory compounds.

Further provided are kits containing the Syk inhibitory compounds and/or bone modulating compounds in forms suitable for administration. The compounds and agents may be in dosage units for ease of administration, or where in liquid form, supplied with dosing devices (e.g., syringes, graduated pipettes, measuring cups, etc.) for administering a proper dose. The kits can also contain descriptions and illustrations in various mediums (e.g., compact discs, video, memory cards, and printed forms) for instructing on proper use of the Syk inhibitors.

5. BRIEF DESCRIPTION OF THE FIGURES

FIG. 1 shows analysis of the hind paws of rats treated with 30 mg/kg of 2,4-pyrimidinediamine compound 1007 in rat collagen induced arthritis (CIA) model. Data are the means±standard error, where n=13 per group, except for naïve (n=4). Radiographs of hindlimbs were obtained at the conclusion of the study and scored blindly. The results show a significant reduction in bone erosion in animals treated with 10 mg/kg (p<0.05) and 30 mg/kg (p<0.001) of the Syk inhibitor.

Figure 2:
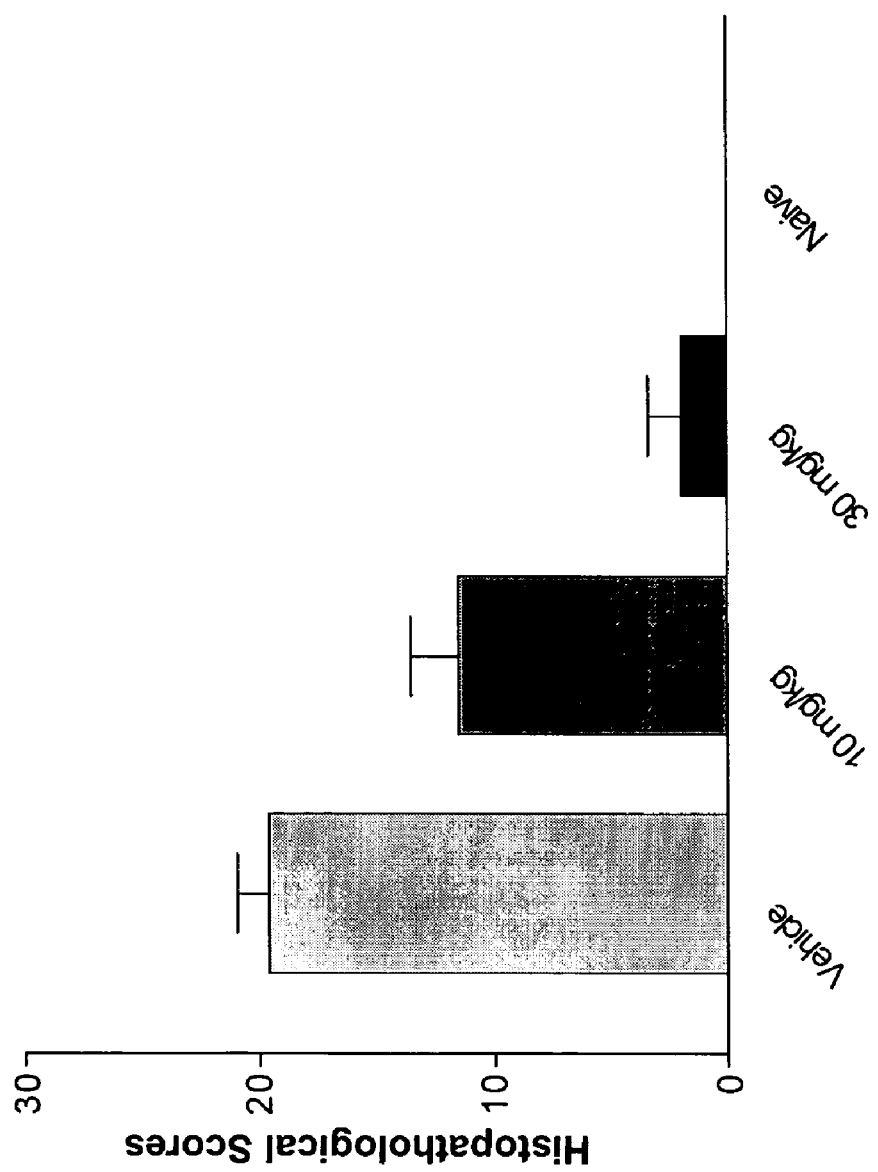

FIG. 2 shows histopathological assessment of bone sections from animals treated with Syk inhibitor compound 1007. Administration of the inhibitor results in significant reduction in severity of bone destruction.

Figure 3:
Figure 3:
Figure 3:
Figure 3:

FIG. 3 shows the reduction in bone erosion, osteoclast activity, and pannus formation in rat collagen induced arthritis upon treatment with 2,4-pyrimidinediamine compound 1007. Upper left—naïve rat; upper right—vehicle rat; lower left—vehicle rat; lower right—compound 1007 treated rat. Micrographs are safranin-O stained sections of hind ankle paws of CIA rats, magnification 40×.

Figure 4:
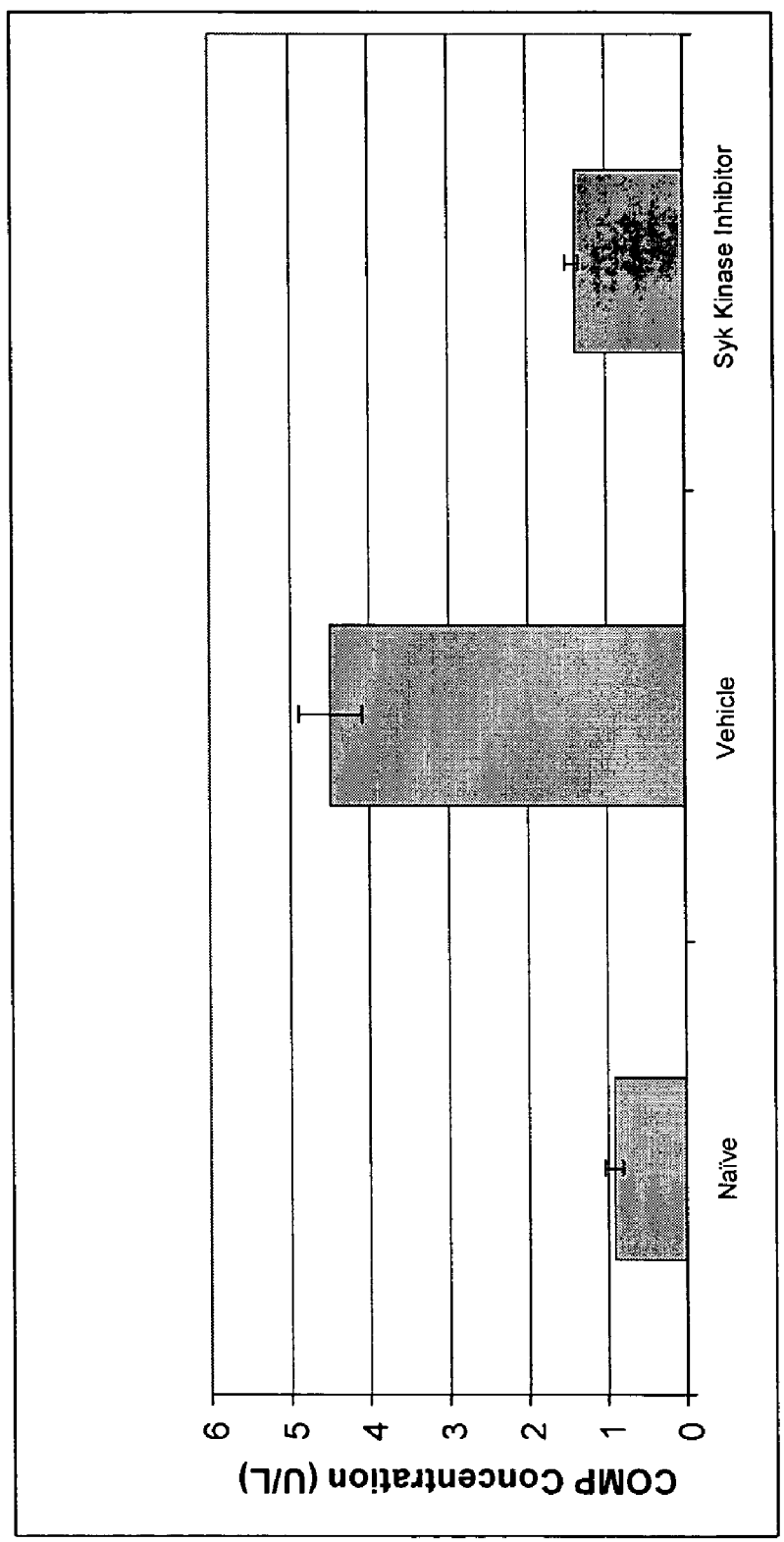

FIG. 4 shows the reduction in serum levels of cartilage oligometrix matrix protein (COMP), a marker for collagen destruction, after treatment of rats with 2,4-pyrimidinediamine compound 1007.

6. DETAILED DESCRIPTION

6.1 Definitions

The terms used in the description herein will have their ordinary and common meaning as understood by those skilled in the art, unless specifically defined otherwise. As used throughout the instant application, the following terms shall have the following meanings:

"Antiresorptive agent" refers to an agent, such as a compound or composition, that attenuates or inhibits bone resorption. The agent can affect any aspect of bone resorption, including, among others, osteoclast development, osteoclast activity, bone matrix structure (i.e., inhibit or slow bone resorption), and enzymes/proteins involved in the resorption process.

"Autoimmune disorder" refers to a condition or disease caused by inappropriate response of an immune system and are commonly associated with nonanaphylactic hypersensitivity reactions (e.g., Type II, Type III, and/or Type IV hypersensitivity reactions) that arise as a consequence of the subject's own humoral and/or cell mediated response to one or more immunogenic substances. Exemplary autoimmune disorders include rheumatoid arthritis, glomerulonephritis, myasthenia gravis, systemic lupus erythematosus, and osteoarthritis.

"Bone formation" and "bone deposition" refers to the process of laying down of new bone material. The osteoblast is the primary cell responsible for forming the bone organic matrix and incorporation of hydroxyapatite crystals during mineralization of the matrix. As such, bone formation encompasses the synthesis of the organic matrix and the mineralization process involving incorporation of hydroxyapatite.

"Bone modulating agent" refers to a compound or composition capable of reducing bone loss, increasing bone mass, and/or increasing bone structural integrity (i.e., strength of bone). The effect of these agents is to decrease the fracture risk. Bone modulating agents encompass antiresorptive agents and osteo-anabolic agents. It is to be understood that the terms "antiresorptive agent" and "osteo-anabolic agent" are not meant to be limiting since some agents may have both antiresorptive and osteo-anabolic properties. The classification of agents in one group or the other reflects the current state of knowledge about the properties of the agents in relation to bone metabolism and is not meant to limiting.

"Bone resorption" refers to the process of bone removal or dissolution. The osteoclast is the primary cell responsible for dissolution of the bone matrix.

"Bone mineral content" refers to the bone mass expressed as bone mass per cm of bone. It is generally used in some embodiments to assess the amount of bone accumulated prior to cessation of bone growth.

"Bone mineral density" or "Bone density" or "BMD" refers to the bone mass in a given area or volume of bone, and is used as a measure of bone health and in the diagnosis of degenerative bone disorders. As is known in the art, the bone mineral density is dependent on the procedure used to determine bone density. Mass per area is areal bone mineral density and is generally expressed in $gm/cm^2$. DEXA and ultrasound are examples of areal bone density measurement techniques. Mass per volume is a volumetric bone mineral density and is generally expressed in $gm/cm^3$. Quantitative computed tomography and magnetic resonance imaging are examples of volumetric bone density measurement techniques. Because the bone mineral density varies with the technique used, the density measurements are translated into "T" and "Z" scores as defined by the World Health Organization (WHO). The T-score is a comparison of a subject's bone mineral density to that of a reference standard, which is generally set as a normal, healthy 30-year-old subject. The Z-Score is a comparison of a subject's bone mineral density to an age and sex matched standard.

"Degenerative bone disorder" refers to a disease or condition characterized by a decrease in bone mass and/or an increase in probability of fractures because of compromised structural integrity of the bone. Many degenerative bone disorders arise from an imbalance between bone formation and bone resorption. This imbalance can be caused by a reduction in osteoblast mediated bone formation, an increase in osteoclast mediated bone resorption, or a combination of changes to osteoblast and osteoclast activity.

"Endocrinopathy" refers to a disease or condition of abnormal secretion of a hormone. Abnormal is meant an increase or decrease in levels of a specified hormone that can give rise to a medical condition. An endocrinopathy is not limited to dysfunction of an endocrine gland but applies to an abnormality in the secretion of a hormone by any cell or organ.

"Estrogen deficiency" refers to a decrease in estrogen levels that is capable of leading to a medical condition associated with the low estrogen levels, but which may or may not have actually resulted in clinical or other diagnostic presentation of the condition.

"Estrogen receptor modulator" refers to a compound that acts on the estrogen receptor by producing estrogen agonist and antagonistic effects. Estrogen receptor modulator initiates signal transduction cascades dependent on the estrogen receptor. An exemplary estrogen receptor modulator is 17β-estradiol. A "selective estrogen receptor modulator" or "SERM" is distinguished from estrogen receptor agonists and antagonists in that the action of SERMs is different for various tissues. Without being bound by theory, different cells differentially express the various estrogen receptor subtypes (e.g., α and β homodimers and α/β heterodimers), which act by suppressing and/or stimulating expression of particular sets of genes. SERMs have differing affinities to the estrogen receptor isoforms, and therefore can have differential effects on particular tissue type. Thus, a SERM can be used to selectively inhibit or stimulate estrogen-like action depending on the tissue. Exemplary SERMs include, among others, clomifene, raloxifene, tamoxifen, toremifene, bazedoxifene, and lasofoxifene.

"Heritable genetic abnormality" refers to a disorder or medical condition arising from the effects of an altered gene or a combination of genes. A heritable genetic disorder is distinguished from genetic changes in somatic cells by the presence of the changes in the gametes (i.e., sperm and/or oocyte) of the subject's parents or early in embryogenesis such that the germline mutations are capable of being pass on to descendants. On the other hand, somatic mutations do not generally pass to descendents. Heritable genetic abnormality as used herein includes single gene abnormalities, where a mutation(s) occurs in a single gene; multigenic disorders, where the disorder is a consequence of mutations in multiple genes; and chromosomal disorders, where the disorder is a consequence of large-scale changes in chromosome structure (e.g., duplications, inversions, insertions, translocations, amplifications, etc.).

"Menopause" and "menopausal" refers to the stage of the human female reproductive cycle that occurs as the ovaries decrease estrogen and progesterone production, causing the reproductive system to gradually stop menstruating. The menopausal period can last anywhere from about 6 months to about 8 years. The average onset of menopause is about 50.5 years, but some women enter menopause at a younger or later age. Premature menopause, also called Premature Ovarian Failure, is menopause occurring before the age of 40, and can be characterized by abnormally low levels of estrogen and high levels of FSH in the affected subject. Postmenopausal refers to the period following menopause. Induced menopause occurs when the ovaries are surgically removed (e.g., by bilateral oophorectomy) or are damaged by radiation or drugs. Perimenopause refers to the menopause transition that begins about 6 years before the natural menopause when the levels of hormones produced by the aging ovaries fluctuate leading to irregular menstrual patterns.

"Osteoblastogenesis" refers to the process of differentiation of stem cells and progenitor cells, such as mesenchymal stem cells, into functional osteoblasts.

"Osteoclastogenesis" refers to the process of differentiation of stem cells and progenitor cells, such as monocyte/macrophage progenitor cells, into functional osteoclasts.

"Osteodystrophy" refers to the constellation of bone disorders arising from chronic kidney insufficiency. It can also occur because of congenital abnormalities in the kidney. When the kidneys fail, dialysis is required to keep the subject alive, and consequently, patients with osteodystrophy are usually on dialysis therapy. Thus, "renal osteodystrophy" refers to the constellation of bone disorder resulting from kidney disease and is commonly found in patients undergoing chronic dialysis. Bone disorders associated with osteodystrophy include varying combinations and degrees of osteoporosis, osteomalacia, osteitis fibrosa, and osteosclerosis. Osteitis fibrosa and osteosclerosis usually occur after long-standing kidney failure. Osteoporosis can be present at any time in patients with kidney insufficiency.

"Osteo-anabolic agent" refers to a compound or composition that induces or promotes bone formation. Generally, the primary target of an osteo-anabolic agent is the osteoblast, the cell responsible for deposition of bone, or the cells that gives rise to osteoblasts, such as mesenchymal stem cells. However, osteo-anabolic agents can also include compounds and compositions that alter the substances or cellular products involved in bone formation, such as osteocalcin involved in binding to hydroxyapatite.

"Osteopenia" refers to a decrease in bone mineral density that is not as severe as osteoporosis. Osteopenia is indicated where there is a decrease in bone mineral density, whether or not osteoporosis is present, as detected by a suitable diagnostic procedure, such as a radiographic technique. The WHO defines osteopenia as a bone density between 1 standard deviation and 2.5 standard deviations below the bone density of a reference standard (i.e., generally a healthy young adult of about 30 years old).

"Osteoporosis" refers to a degenerative bone disorder characterized by low bone mass and microarchitectural deterioration of bone tissue, leading to enhanced bone fragility and increased fracture risk. Primary osteoporosis represents bone mass loss unassociated with any other illness and is typically related to aging and age-related loss of gonadal function. Forms of primary osteoporosis are postemenopausal osteoporosis and senile osteoporosis. Primary osteoporosis also includes idiopathic osteoporosis, which is osteoporosis where an underlying or secondary cause of the bone degeneration is unknown. Secondary osteoporosis refers to osteoporosis resulting from another condition or illness besides the age-related bone degeneration encompassed by primary osteoporosis. The WHO defines osteoporosis as bone density 2.5 standard deviations below the bone density of a reference standard (i.e., generally a healthy young adult of about 30 years old).

"Peak bone mass" refers to the maximum amount of bone mass a subject attains in a life span. Typically for humans, the peak bone mass occurs at approximately 30 years of age. The peak bone mass is correlated with the risk of osteoporosis late in life since a high peak bone mass may buffer the decrease in bone mass in the latter stages of life, thereby limiting any increase in fracture risk.

"Syk-dependent signaling cascade" refers to a signal transduction cascade in which Syk kinase plays a role. Non-limiting examples of such Syk-dependent signaling cascades include cell signaling associated with FcαRI, FcεRI, FcγRI, FcγRIII, B-cell receptor (BCR), and integrins.

"Syk kinase" or "Syk" refers to the non-receptor (cytoplasmic) spleen protein tyrosine kinase of about 72 kDa expressed in B-cells and other hematopoietic cells. Syk kinase is characterized a number of structural features, including two consensus Src-homology 2 (SH2) domains in tandem that bind to phosphorylated immunoreceptor tyrosine-based activation motifs ("ITAMs"), a "linker" domain, and a catalytic domain (for a review, see Sada et al., 2001, *J. Biochem.* (Tokyo) 130:177-186 and also Turner et al., 2000, *Immunology Today* 21:148-154 and Wong et al., 2004, *Expert Opin Investig Drugs.* 13(7):743-62.). Syk kinase is also critical for tyrosine phosphorylation of multiple proteins that regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, *Immunity* 16: 547-558). Syk kinase includes kinases from any species of animal, including but not limited to, homo sapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are available from GENBANK. Specific examples of mRNAs encoding different isoforms of human Syk kinase are available at GENBANK accession no. gi|21361552|ref|NM_003177.2, gi|496899|emb|Z29630.1|HSSYKPTK[496899] and gi|15030258|gb|BC011399.1|BC011399[15030258], which are incorporated herein by reference.

6.2 Methods of Treating Degenerative Bone Disorders

Bone remodeling is a complex process involving bone resorption by osteoclasts and bone formation by osteoblasts. To grow or maintain bone mass, there must be an appropriate balance in the rates of bone formation and bone resorption. Any abnormal imbalance between the two processes, such as excessive bone remodeling or a net excess of bone resorption over bone formation, can lead to weaknesses in bone structure and a corresponding increased risk of fractures. The present disclosure provides methods and compositions for treating these degenerative bone disorders as well as prophylactic approaches for preventing bone loss that can lead to increased fracture risk. These methods and compositions are based on the use of Syk inhibitors to attenuate or inhibit osteoclastogenesis and osteoclast activity, thereby decreasing or inhibiting the excessive bone loss associated with abnormal activity of osteoclasts. In addition, in those degenerative bone disorders where inappropriate remodeling results in compromised bone integrity but without significant bone loss, an increase in bone mass resulting from inhibition of bone resorption can increase bone strength sufficiently to decrease the fracture risk. For the purposes disclosed herein, the Syk inhibitory compounds can be used independently or in combination with other modulators of bone remodeling (i.e., anti-resorptive agents and osteo-anabolic agents), for treatment as well as prophylaxis.

In the present disclosure, various degenerative bone disorders can be treated by administering to a subject in need thereof an amount of a Syk inhibitory compound effective to treat the degenerative bone disorder. The diagnosis of a particular disorder can be based on clinical presentations typically used by those skilled in the art to diagnose the disorder. As further discussed herein, other diagnostic criteria such as the presence of biochemical and molecular markers of the disease, can be used independently or as a supplement to the examination of the clinical presentations. Standard diagnostic criteria can be found in various references, including, by way of example and not limitation, the *World Health Organization's International Classification of Diseases,* Tenth Revision (ICD-10); Resnick, D., *Diagnosis of Bone and Joint Disorders,* $4^{th}$ Ed., W.B. Saunders Company (2002); and *AACE Medical Guidelines for Clinical Practice for the Prevention and Treatment of Postmenopausal Osteoporosis:* 2001 Edition, with Selected Updates for 2003. All publications are incorporated herein by reference.

Accordingly, in some embodiments, the Syk inhibitory compounds can be used to treat primary osteoporosis, which is a loss of bone mass unrelated to any other underlying disease or illness. In other words, the loss of bone mass is not caused by another condition, such as hormonal imbalances resulting from a pathological condition or other diseases that indirectly affect bone metabolism. Two general types of primary osteoporosis are described in the art. Type I, also referred to as high turnover or postmenopausal osteoporosis, is correlated with a decrease in hormone levels secreted by the ovaries in the postmenopausal period. The exact etiology of the disease has not been completely resolved. The condition occurs in about 5 to 20% of the female population, and gives rise to an increased fracture risk. The disease affects females because they undergo a rapid loss of bone mass beginning at menopause and lasting for about 4 to about 8 years, followed by a more gradual bone loss later in life. Type II, also referred to as low turnover or senile osteoporosis, can arise when the processes of bone resorption and bone formation are not coordinated such that there is a net excess of bone resorption over bone formation. Whereas Type I osteoporosis occurs primarily in women, Type II osteoporosis can occur in women and men with equal frequency. Thus, some women can have both Type I and Type II osteoporosis.

Other forms of primary osteoporosis are idiopathic osteoporosis, an osteoporotic condition where there is no identifiable cause for the bone loss. Idiopathic osteoporosis can affect children and adults. Juvenile osteoporosis is osteoporosis occurring in children between the ages of about 8 and about 14 years of age. In juvenile osteoporosis, impairment of bone growth occurs over a period of several years, and in most cases, goes into remission. However, the period of impaired bone growth and remodeling can lead to skeletal deformations, such as curvature of the spine and short stature. Moreover, inadequate accumulation of bone mass could lead to an increased risk of fractures later in life.

In some embodiments, the Syk inhibitory compounds can be used to treat degenerative bone disorders arising from a secondary condition, where the bone degeneration is a consequence of the underlying medical condition or disease. In some embodiments, specifically excluded from the treatments herein is bone degeneration occurring because of dysregulation of immune system activity. These include autoimmune diseases that promote bone destruction and diseases that target organs indirectly affecting bone metabolism. Exemplary autoimmune diseases associated with bone destruction are rheumatoid arthritis and osteoarthritis. Rheumatoid arthritis is a chronic inflammatory disease involving the synovial membranes and atricular structures of the joints. Exemplary autoimmune diseases affecting organs involved in regulating bone metabolism are glomerulonephritis and membrane glomerulonephritis. Glomerulitis refers to a specific set of renal diseases in which an immunologic mechanism triggers inflammation and proliferation of glomerular tissue. Immune complexes deposited or formed in the glomeruli trigger a chronic inflammatory reaction leading to compromised kidney function. Because the kidney is the key organ for production of the active form of vitamin D, namely 1,25-dihydroxycholecalciferol, and is responsible for regulating calcium and phosphate levels in the blood, kidneys damage results in the inability to absorb intestinal calcium and a corresponding increase in parathyroid hormone level, which induces calcium mobilization from the bone. Similarly, membranous glomerulonephritis is an immune related disease in which immune complexes formed via binding of antibodies to glomerular basement membrane antigens activate a response of the complement system that acts on the glomerular epithelial cells. The complexes in turn stimulate release of proteases and oxidants that damage the capillary walls, comprising the integrity of the glomeruli.

In some embodiments, also specifically excluded from the methods herein is treatment of certain oncogenically induced osteoporosis, which refers to bone loss arising from tumors, both benign and metastatic. Tumors can affect bone remodeling by various mechanisms, including, among others, releasing factors that affect osteoclast or osteoblast activity, crowding and destroying cells involved in bone metabolism, effects on hormone secretion (e.g., estrogen and parathyroid hormones), and adverse effects on organs involved in calcium metabolism. Exemplary tumors known to have a high predilection for metastasizing to bone are breast, prostrate, lung, and kidney cancers. Each of these tumors can cause bone loss by any one or more of the processes discussed above. For example, breast cancer can accelerate bone resorption by producing factors that stimulate osteoclast development, such as IL-1, IL-6, TGFα, and tumor necrosis factor (TNF). Breast cancer cells are also known to produce parathyroid hormone-like protein (PTHrP), which binds PTH receptor and induces hypercalcemia, activates osteoclast activity, and increases renal absorption of calcium and excretion of phosphate.

Hematopoietic neoplasms, such as myeloid and lymphoid neoplasms, can also affect bone integrity by producing factors that regulate osteoclast and osteoblast development, destroying osteoclasts and osteoblasts in the bone marrow, and by differentiating into cells involved in bone remodeling. For example, in multiple myeloma, myeloma cells secrete TNF-α, TNF-β, RANKL, IL-1, and IL-6, all of which are known to affect osteoclast development and bone resorption. As an indication of this effect, osteoclasts can be found near the myeloid tumor cells but not in parts of the bone where the myeloid tumor cells are absent.

In accordance with the above, the Syk inhibitory compounds can be used to treat degenerative bone disorders caused by various secondary conditions. In some embodiments, the Syk inhibitory compounds can be used to treat bone loss caused by an endocrinopathy, a condition characterized by abnormal hormone secretion. Abnormal hormone secretion can be either an increase or reduction in hormone levels. Various hormones can affect bone metabolism, including but not limited to, estrogen, testosterone, growth hormone, calcitonin, parathyroid hormone, parathyroid hormone related protein, glucocorticoids, and calcitriol. Decrease in levels of estrogen, testosterone, human growth hormone, calcitriol, human growth hormone, and calcitonin can lead to a net excess of bone resorption over bone formation. Increases in parathyroid hormone, parathyroid hormone related protein, and glucocorticoids can also lead to a net excess of bone resorption over bone formation. Thus, pathological conditions of endocrine glands resulting in a decrease or an increase in particular hormones can cause bone loss and increased fracture risk.

Various forms of endocrinopathies are associated with loss of bone mass and corresponding bone degeneration. In some embodiments, the Syk inhibitory compounds can be used to treat bone degeneration arising from hypercorticolism or an abnormal increase in the production of glucocorticoids by the adrenal glands (e.g., Cushing's syndrome). Endogenous overproduction of glucocorticoids can arise from primary adrenal lesions, such as adrenal adenoma, adrenal carcinoma, or nodular adrenal hyperplasia. These forms of hypercorticolism are independent of adrenocorticotropic hormone (ACTH). Hypercorticolism can also arise from excessive production ACTH by the pituitary gland and consequent stimulation of the adrenal cortex to secrete glucocorticoids. In some instances, small cell lung tumors or carcinoid tumors can overproduce ACTH and stimulate secretion of glucocorticoids.

In some embodiments, the endocrinopathy associated with bone degeneration is hypogonadism. This condition manifests differently in males and females and is characterized by absent or decreased function of the testis in the male and the ovaries in the female. Some forms of hypogonadism can arise through disruption of the hypothalamic-pituitary-gonadal regulatory pathway. The hypothalamus releases pulses of luteinizing hormone-releasing hormone (LHRH), also termed gonadotropin-releasing hormone (GnRH)) into the hypothalamic-pituitary portal system. In response to these pulses of LHRH, the anterior pituitary secretes follicle-stimulating hormone (FSH) and luteinizing hormone (LH), which in turn stimulate gonadal activity. As part of the feedback regulatory mechanism, the increase in gonadal hormones results in lowered FSH and LH secretion at the pituitary level. In the testes, LH stimulates Leydig cells to secrete testosterone, while FSH is necessary for tubular growth. In the ovaries, LH acts to induce production of progestins and androgens, while FSH acts upon granulosa cells to stimulate aromatization of these steroid precursor to generate estrogen. Hypogonadism can occur when any part of the hypothalamic-pituitary-gonadal connection is disrupted. Hypogonadism can be primary hypogonadism, where the ovaries or testes do not function or are absent, or central hypogonadism, where the hypothalamic production of luteinizing releasing hormone is disrupted. In other situations, hypogonadism can arise when the pituitary gland fails to secrete luteinizing hormone or follicle stimulating hormone. As further discussed below, hypogonadism encompasses gonadal dysgenesis that arises from mutations affecting development of the gonads. The most common form of hypergonadotropic hypogonadism in males is Klinefelter syndrome. The most common form of hypergonadotropic hypogonadism in females is Turner syndrome. In some embodiments, the loss of gonadal function is by surgical intervention, such as an ovariectomy or orchiectomy, as further discussed below.

In other embodiments, the endocrinopathy is hyperparathyroidism, a condition characterized by excess secretion of parathyroid hormone (PTH). This hormone regulates calcium and phosphorous homeostasis by raising serum calcium and lowering serum phosphorous levels. The hormone also stimulates osteoclasts to increase bone resorption. PTH also acts indirectly through the stimulation of adenyl cyclase to increase renal tubular calcium resorption and phosphate excretion. Finally, PTH activates the conversion of 25-hydroxyvitamin D to 1,25-dihydroxyvitamin D, the active form of vitamin D that stimulates calcium and phosphate absorption from the gastrointestinal tract. Hypercalcemia results from excess release of PTH.

Two general forms of hyperparathyroidism are described based on clinical presentations. Primary hyperparathyroidism, which is overproduction of parathyroid hormone by the thyroid gland, may result from an adenoma of the parathyroid gland, hypertrophy of the parathyroid gland, or malignancies of the parathyroid gland. Parathyroid gland neoplasias giving rise to hyperparathyroidism is frequently associated with multiple endocrine neoplasias MEN1 and MEN2A. Secondary hyperparathyroidism can develop when there is hyperplasia following long-term stimulation of the parathyroid gland in response to low calcium levels. Thus, secondary hyperparathyroidism is prevalent in subjects with chronic renal failure, rickets, and calcium maladsorption. Unlike primary hyperparathyroidism, which is generally characterized by hypercalcemia, secondary hyperparathyroidism is generally not associated with hypercalcemia. With continued long-term stimulation by low calcium levels, the parathyroid gland continues to secrete high levels of PTH regardless of whether the hypocalcemia is resolved, leading to a condition generally referred to as tertiary hyperparathyroidism.

Conversely, bone degeneration abnormalities can occur in subjects with decreased secretion or activity of PTH, namely hypoparathyroidism. This condition is found less frequently than hyperparathyroidism and can be caused by congenital disorders (e.g., parathyroid aplasia, DiGeorge syndrome, etc.), iatrogenic causes (e.g., removal of the parathyroid glands during thyroid or parathyroid surgery, radiation, etc.), and infiltration of the parathyroid glands (e.g., metastatic carcinoma, Wilson's disease, sarcoidosis, etc.). Hypoparathyroidism can also result from secretion of inactive forms of PTH or from attenuated response to PTH by bones and kidneys, but these conditions are generally rare occurrences. At the physiological level, low PTH activity can cause hypocalcemia and hyperphosphatemia. The reduction in calcium absorption and increased bone mobilization arising from low PTH can lead to bone degeneration, which can be treated by Syk inhibitory compounds.

In some embodiments, the Syk inhibitory compounds can be used to treat osteodystrophy, a degeneration of bone resulting from compromised kidney function. Clinical presentations of osteodystrophy can be in the form of osteoporosis, osteomalacia, osteitis fibrosa, osteosclerosis, osteomalacia, and secondary hyperparathyroidism. Subjects with chronic kidney failure develop these conditions because of associated imbalances of hormones that affect bone metabolism and calcium balance. For example, renal dysfunction leads to hyperphosphatemia and hypocalcemia, thereby leading to secondary hyperparathyroidism. This condition is compounded by a decrease in the ability to form 1,25-dihydroxyvitamin D3 in the dysfunctional kidney. This vitamin deficiency can lead to osteomalacia, a hypomineralization of trabecular and cortical bone following the cessation of bone growth. In some forms of osteomalacia, deposition of aluminum introduced from dialysate solutions, antacids, or aluminum-containing phosphate-binding agents used to combat the hyperphosphatemia can further compromise bone formation. Common causes of kidney failure include, among others, diabetes, high blood pressure, glomerulonephritis, polycystic kidney disease, kidney obstructions, and kidney infections (e.g., pyelonephritis). Many cases of kidney failure, however, are idiopathic, with no identifiable cause of renal dysfunction.

Although dialysis treatment is able to eliminate the toxic waste products that accumulate with renal failure, the inability to synthesize 1,25-dihydroxyvitamin D3 and the continuing hypocalcemic condition leads in many instances to continued release of parathyroid hormone and consequent bone dissolution. Thus, the Syk inhibitory compounds can be useful for patients undergoing dialysis treatment to attenuate any excessive bone resorption and limit bone loss.

In some embodiments, the bone degeneration treatable with the Syk inhibitory compounds can be bone loss associated with destruction of one or both of the gonads, such as by surgery (i.e., ovariectomy or oophorectomy). Ovariectomies are performed for a variety of medical reasons, including presence of ovarian or uterine tumors, removal of ovarian cysts, as a prophylactic measure to reduce breast cancer risk, for treatment of pelvic pain caused by endometriosis, removal of embryo implanted in the ovary, and treatment of pelvic inflammatory disease. In many instances, a percentage of subjects who have hysterectomies to treat uterine fibroids, uterine cancer, endometriosis, uterine prolapse, and excessive uterine bleeding, also undergo an ovariectomy. As discussed above, loss of the ovaries results in a sudden decrease in estrogen levels and other hormones, mimicking the physiological conditions of menopause. Consequently, the risk of osteoporosis increases significantly in females who have undergone an ovariectomy. Although estrogen or other hormone replacement therapies compensate for some of the consequences of estrogen decrease, this may not prevent development of osteoporosis, which may be accelerated in ovariectomized individuals. Treatment with Syk inhibitory compounds can be used to ameliorate the bone loss associated with the removal of ovaries.

Loss of the testes by orchiectomy or hypogonadism induced by GnRH agonist treatment can lead to osteoporosis in men. This is apparently due, in part, to the decrease in androgen production. Without being bound by theory, androgens may function in maintaining cancellous bone mass and integrity, regardless of age or sex. Replacement therapy with doses of testosterone has been shown to increase bone mineral density. With continuous, long-term hormone replacement therapy, bone density can be maintained at normal levels (Katznelson et al., 1996, *J. Clin Endocrin. Metab.* 81:4358-4365). Syk inhibitor compounds, either alone or in combination with androgen therapy, could also be used to inhibit or reduce bone loss associated with orchiectomy.

In some embodiments, the methods can be directed to use of the Syk inhibitory compounds to treat bone degeneration associated with heritable genetic disorders. Inherited genetic disorders can arise from, among others, single gene inheritance, multifactorial or polygenic inheritance, chromosome abnormalities, and parental imprinting abnormalities. Various inherited genetic abnormalities affecting bone metabolism have been identified, including, osteogenesis imperfecta, homocystinurea, gonadal dysgenesis, and hypophosphatasia.

In accordance with the above, in some embodiments, the Syk inhibitory compounds can be used to treat osteogenesis imperfecta (OI), a heritable disorder displaying a broad range of clinical manifestations, with common characteristics of low bone mass and high frequency of fractures. Osteogenesis imperfecta comprises at least seven different conditions based on clinical presentation and bone structure. Type I is a mild form where afflicted subjects attain normal height but show higher than normal incidence of fractures that decreases after puberty. Type II is the most severe form, typically resulting in death in the perinatal period. Subjects with this form of OI have multiple fractures and show severe skeletal deformities, and a concomitant decrease in cortical and trebecular bone thickness. Type III disorders display skeletal deformities from birth and result in multiple fractures because of the fragile nature of the bones. Type IV disorders show a diverse set of clinical presentations and include phenotypic characteristics that do not fall within Types I-III. Skeletal deformities and fractures are common. Type V forms show moderate deformities and moderate to severe bone fragility. Afflicted subjects in this class display hypertrophic callus formation at fracture sites, calcification of interosseuous membranes, and presence of X-ray opaque regions adjacent to the growth plates. The lamellar bone shows a mesh-like appearance. Type VI disorders show moderate to severe skeletal deformity, excessive osteoids, and a distinctive fish-scale shaped appearance of the lamellar bone. Type VII form shows moderate to severe skeletal deformity and bone fragility and shortening of the humerous and femur. Type I-IV osteogenesis imperfecta is associated with mutations in the type I collagen genes. Current treatments for osteogenesis imperfecta employ antiresorptive bisphosphonates to strengthen the bone by limiting bone resorption. This treatment may not improve the quality of the bone but may increase bone mass sufficiently to decrease the probability of fractures and decrease the pain associated with the disease. The use of Syk inhibitors can provide similar therapeutic benefits by limiting bone resorption and thereby increasing strength of the bone.

In some embodiments, the heritable genetic disorder that can be treated with the inhibitor compounds is homocystinuria. This genetic abnormality arises from high levels of the amino acid homocysteine in the blood and can be caused by a deficiency of the enzymes that convert the amino acid methionine to amino acid cysteine or a deficiency in the conversion of homocysteine to methionine. Mutations in the enzyme cystathionine beta-synthase (CBS) represent the most common form of homocystinuria. This enzyme acts in the transsulfuration pathway where homocysteine condenses with serine to form cystathionine in a rate-limiting reaction catalyzed by the B6-dependent CBS enzyme. The cystathionine is then converted to yield cysteine. The inability to convert homocysteine results in accumulation of homocysteine. The physiological effects of homocystinuria are pleiotropic, with afflicted subjects displaying a multitude of symptoms, such as increased risk of thrombosis, atherosclerosis, dislocation of the lens, thin build with long limbs, arachnodactyly (spidery fingers), and sciolosis (curvature of the spine). The disease is also characterized by osteoporosis and increased risk of fractures. Without being limited by theory, increased levels of homocyteine is thought to interfere with the crosslinking of collagen in the bone (Lubec et al., 1996, *Biochim. Biophys. Acta* 1315:159-62). Although inhibiting bone resorption may not affect the quality of the organic matrix, limiting bone loss by use of Syk inhibitory compounds, independently or in combination with antiresorptive agents and/or osteo-anabolic agents, can provide sufficient increases in bone strength to reduce the incidence of fractures.

In some embodiments, the inhibitor compounds can be used to treat hereditary forms of gonadal dysgenesis, a clinical condition in which the development of the fetal gonad is abnormal. As discussed above for hypogonadism, absence or insufficient gonadal function can lead to osteoporotic condition due to hormonal imbalances. Gonadal dysgenesis typically results from chromosomal abnormalities that lead to failure of the gonads to develop properly. The most prevalent form of gonadal dysgenesis is Turner's syndrome, a disorder affecting females in which one of the two X chromosomes is missing or incomplete. However, the disorder can also arise from mutations in genes that regulate gonadal differentiation and testis determination. For example, mutations in the sex-determining gene SRY, which encodes a transcription factor of the high mobility group (HMG) family, cause Swyer's syndrome, also referred to as pure XY gonadal dysgenesis. Subjects with the SRY mutation are phenotypic females but display a XY karyotype, and consequently do not develop secondary sexual characteristics at puberty nor menstruate. Another form of gonadal dysgenesis occurs from deficiencies in CYP 17, a 17-α-hydroxylase involved at key points in steroid biosynthesis. Subjects with deficiencies in the hydroxylase are female regardless of whether they are XX or XY because of the inability to synthesize androgens and estrogens prenatally and postnatally. Because of abnormally low estrogen and gonadotrophin levels in subjects with gonadal dysgenesis, there is an increased incidence of osteoporosis and associated bone fractures. Current therapies for gonadal dysgenesis include, among others, administration of estrogen and growth hormone therapy. In addition to such therapies, reducing bone loss by use of Syk inhibitors can decrease the degree of osteoporosis that occurs in these patients.

Another inherited degenerative bone disorder that may be amenable to treatment with the methods herein is hypophosphatasia. Recognized in the art are at least six forms of hypophosphatasia. Perinatal (lethal) hypophosphatasia is the most severe form and is expressed in utero. In surviving neonates, there is undermineralization and poor ossification of the bone. Infantile hypophosphatasia presents clinical manifestations before 6 months and is characterized by rickets-like bone deformities, hypomineralization, hypercalcemia, and renal dysfunction. Childhood hypophosphatasia is characterized by premature loss of teeth, and shows skeletal deformities such as bowed legs, enlarged metaphysis, short stature, and non-progressive myopathy. Adult hypophosphatasia shows clinical manifestations during middle age, common attributes being premature loss of teeth, rickets-like symptoms, osteomalacia, high frequency of fractures, hyperparathyroidism, and abnormal calcium pyrophosphate deposition. Odontohypophosphatasia, which is another form of hypophosphatasia, is diagnosed where there is dental disease, such as early onset of periodontal disease, but is unaccompanied by any associated symptoms of rickets or osteomalacia. Finally, pseudohypophosphatasia is a rare form of hypophosphatasia in which the level of detectable alkaline phosphatase is normal or increased. The phosphatase enzyme in pseudohypophosphatasia is inactive at physiological pH but is active under test conditions used to detect alkaline phosphatase activity.

Despite the different symptoms of the disease, hypophosphatasia also share many clinical manifestations. These include increased blood and urine levels of phosphoethanolamine, pyridoxal-5-phosphate, and pyrophosphate; consistent subnormal levels of serum alkaline phosphatase; radiological changes of bone structure; and abnormal levels of unmineralized bone. Although hypophosphatemia is associated with altered alkaline phosphatase activity, the disorder is not limited to defects in the alkaline phosphatase enzyme. As suggested by recent molecular analysis, mutations in a Zn-metalloendopeptidase (PHEX) expressed in bone and cartilage is associated with X-linked hypophosphatemic rickets (HYP), while mutations in fibroblast-growth-factor 23 is associated with autosomal-dominant hypophosphatemic rickets (ADHR) (Rowe, 2004, *Crit. Rev. Oral Bio.l Med.* 15(5):264-81). Regardless of the molecular causes of the disorder, the Syk inhibitory compounds can be used to attenuate or inhibit bone resorption and increase bone deposition, thereby ameliorating some of the symptoms of the disorder.

In some embodiments, the Syk inhibitor compounds can be used to treat Paget's Disease, also known as osteitis deformans. It affects both males and females, and is commonly diagnosed in patients 50 or more years of age. Although symptoms are variable, clinical presentations include skeletal pain, skeletal deformities, increased bone fractures, and deafness. Commonly affected bones are the pelvis, collarbone, spine, skull, lower leg, thigh bones, and the humerus. In Paget's disease, excessive bone remodeling is found in localized regions. The initial stage of the disorder is characterized by increased bone resorption in a focal region, with an osteolytic lesion being a commonly detected abnormality upon radiological examination. The osteoclasts are larger than normal adult osteoclasts and show a higher number of nuclei. The excessive bone resorption is followed by an increase in bone formation, a stage characterized by increased number of normal appearing osteoblasts. The rapidly deposited bone, however, is structurally disorganized in appearance, being soft and porous in character, which accounts for the skeletal deformations and increased fracture risk. Reflecting the increased rate of bone remodeling, there are elevated levels of serum alkaline phosphatase and urinary excretions of hydroxyproline and pyridinoline. Because Paget's Disease is considered primarily a disorder of the osteoclast, inhibiting osteoclastogenesis and osteoclast activity based on Syk inhibition can provide a therapeutic approach to treating the degenerative effects of this disorder.

In some embodiments, the degenerative bone disorder treated is periodontal disease. Periodontal disease is believed to arise from an opportunistic infection by indigenous plaque forming bacteria followed by a time-dependent immune response that includes the remodeling of the subjacent connective tissues and bone. Although the exact disease mechanism is unknown, bacteria can release various endotoxins and lipopolysaccharides that ultimately activate osteoclast activity. These bacterial factors may act to induce host immune cells to release extracellular factors capable of stimulating osteoclastogenesis and/or inducing osteoblasts to release factors involved in recruitment and activation of osteoclasts. Various endotoxins may also inhibit bone formation by inhibiting osteoblastic collagen synthesis and by preventing development of osteoblasts. The end result is an imbalance between bone resorption and bone formation and a corresponding degeneration of the bone supporting the teeth, which ultimately leads to loss of teeth. By inhibiting osteoclast activity, the rate of resorption of bone may be inhibited or attenuated, thereby preventing the complications associated with periodontal disease.

It is to be understood that the use of Syk inhibitors are not limited to the degenerative bone disorders described herein, but may be applied to degenerative bone disorder characterized by a net excess of bone resorption over bone formation. This condition may arise from increased osteoclastogenesis, increased osteoclast activation, decreased osteoblastogeneis, decreased osteoblast activity, or a combination of increased osteclastogenesis and decreased osteoblastogenesis. Thus, the methods herein encompass treatments for degenerative bone disorders generally in which there is an imbalance of bone resorption over bone formation.

In addition to the treatment of degenerative bone disorders, the Syk inhibitory compounds can be used, either independently or in combination with bone modulating agents, as prophylaxis to prevent bone loss in subjects at risk of bone loss and increased fracture risk. There are a number of risk factors for developing osteoporosis and other degenerative bone disorders. In the human population, the two significant risk factors are age and gender. With increasing age, the bone mass density of both males and females decrease because of a decrease in the number of osteoblasts recruited to bone erosion regions and the shorter replicative lifespan of osteoblasts. This slow process of bone loss is common for both males and female. However, in females, the sudden drop in estrogen levels during menopause accelerates bone remodeling that lasts for about 4-8 years. The drop in estrogen appears to result in increased osteoclast activity, decrease in survival of osteocytes, and decreased sensitivity to mechanical stimuli. Accordingly, as prophylactic treatment to prevent or reduce the occurrence of bone loss, the Syk inhibitory compounds can be given to females of age of about 35 yrs or older, 45 yrs or older, 55 yrs or older, or 65 yrs or older. Females in the menopausal or postmenopausal period may benefit from the treatments in limiting bone loss arising from the decrease in estrogen levels. For males, the compounds can be given to limit bone loss in subjects of age of about 35 years or older, 45 yrs or older, 55 yrs or older, and 65 yrs or older. Prophylactic treatments can be warranted for both males and females whose bone mass density is less than about $50^{th}$ percentile, less than about $40^{th}$ percentile, less than about the $30^{th}$ percentile of the mean bone mineral density of the population in the age group to which the subject belongs. These include the age groups of 35 to 44 yrs, 45 to 54 yrs, 55 to 65, 65 to 74 yrs, and 75 yrs or older.

In other embodiments, the treatments can be directed to subjects with one or more risk factors for bone loss, where the risk factor is other than the age or gender of the subject. Loss of bone mineral density is correlated with a number of external factors, such as nutrition, living habits, geographic ancestry (e.g., Caucasian ancestry), and family history. Dietary deficiency in calcium, from malnutrition, cultural dietary habits, or eating disorders, can result in lower bone mineral density. The likelihood of such individuals developing osteoporosis increases because of the lower amount of accumulated bone at the beginning of the age-related or menopausal-related imbalance of bone resorption over bone formation. The important factors influencing osteoporosis risk are peak bone mass and the rate at which bone is lost in later life. If the peak bone mass is lower than the average of the population group to which the subject belongs, the subject is likely at risk for osteoporosis. Thus, the Syk inhibitory compounds can be used for those subjects whose dietary intake has been insufficient such that they are at increased risk for developing a degenerative bone disorder. As used herein, a low dietary calcium is intake that falls below the recommended daily allowance needed to attain sufficient peak bone mass and/or limit bone loss. Such recommendations are given in the National Institutes of Health Consensus Development Conference, Optimal Calcium Intake, NIH Consensus Statement Online 1994 Jun. 6-8; 12(4): 1-31 (incorporated herein by reference). The following optimal daily intake of calcium is recommended: infants who are 6 months or younger, 400 mg; infants who are 6 months to 1 year old, 600 mg; children who are 1 to 5 years old, 800 mg; children who are 6 to 10 years old, 800-1200 mg; adolescents and young adults who are 11 to 24 years old, 1200 to 1500 mg; males who are 25 to 64 years old, 1000 mg; males who are 65 years or older, 1500 mg, females who are 25-50 years old, 1000 mg; females who are 50 years or older and on estrogen therapy, 1000 mg; females who are 50 years or older not on estrogen therapy, 1500 mg; females who are 65 years or older, 1500 mg; pregnant and nursing females, 1200 to 1500 mg. It is to be understood that insufficiency of calcium intake is measured in periods of months to years, for instance 6 months or more, where the low calcium intake is a level that is correlated with bone mineral density that falls below the level required to prevent the negative consequences of bone loss occurring with increasing age.

In some embodiments, the risk factor associated with bone loss is tobacco use. Tobacco smoking is correlated with lower bone mineral density in a number of studies (Sewon et al., 2004, *Arch Oral Biol.* 49(5):355-8; MacInnis et al., 2003, *J Bone Miner Res.* 18(9):1650-6). Moderate smokers (1-10 cigarettes/day) and heavy smokers (>10 cigarettes/day) show lower bone density than nonsmokers, with heavy smokers having a significantly lower bone density than those who do not smoke (Sewon, supra). Prophylactic treatment with the Syk inhibitory compounds can be directed to subjects who use tobacco at an amount sufficient to decrease bone mineral density as compared to nonsmokers of the same age group. Tobacco use refers to use of various forms of tobacco, including smoked tobacco, such as cigarettes, cigars, and pipe tobacco. Tobacco also includes smokeless tobacco, such as snuff and chewing tobacco, both of which appear to be correlated with decreased bone mineralization density (Spangler et al., 2001, *Med Hypotheses* 56(5):553-7).

In some embodiments, the risk factor associated with bone loss is inadequate physical exercise. Immobility and prolonged bed rest can induce hypercalciurea and bone loss. In contrast, weight-bearing stress on the bones in the absence of muscle activity can maintain bone mass (Todd et al., 2003, *Postgrad Med. J.,* 79:320-323). Thus, with weight-bearing physical exercise, bones adjust to the regularly applied mechanical force by increasing bone mineralization density. A weight-bearing exercise is any physical activity that places sufficient mechanical load on the bones to maintain or increase bone mineralization density. For example, swimming has little impact on bone mineralization density while activities such as walking and gentle aerobic exercise protects against further loss of bone. Weight training or high impact aerobic exercises, such as running, can increase bone mineralization density in the hip and lumbar spine. Thus, the treatments herein may be appropriate for subjects who are sedentary and/or have inadequate mechanical stress on the bones to maintain or increase bone mineralization density.

In other embodiments, the risk factor associated with bone loss is a family history of low bone density or degenerative bone disorders, such as osteoporosis. From studies of twins and other sibling studies, there is a hereditary factor to bone mineralization density. For example, twins have a closer relationship in regards to bone density than dizygotic twins, and studies of families of osteoporotic subjects tend to have low bone density, with a high correlation in the bone density of osteoporotic men and their children. The low bone density is not correlated with any identifiable environmental factor common in the families, thus pointing towards a genetic factor. Because the peak bone density corresponds to the probability of osteoporosis in the later stages of life, individuals with a family history of low peak bone density is at increased risk for developing osteoporosis.

It is to be understood that the risk factors for evaluating the suitability of prophylactic therapy is not limited to a single risk factor, but will take into account a combination of the risk factors known or suggested as correlating with low bone mineralization density and degenerative bone disorders.

6.3 Diagnosis of Degenerative Bone Disorders and Tests for Bone Resorption/Turnover Degenerative bone disorders and osteoporotic condition can be detected and diagnosed using standard methods known in the art. These include clinical assessment of the subject and/or measurement of biochemical and molecular markers correlative of bone metabolism and bone loss.

In some embodiments, the basis for diagnosis of a degenerative bone disorder can be the bone mineral density. To take into account differences in various diagnostic techniques used to measure bone mineral density, the absolute measured value is compared to a set standard criteria, such as that promulgated by the World Health Organization (WHO). Under the WHO standard, the measured bone mineral density is expressed in relative terms as "T" and "Z" scores. A "T" score corresponds to the fracture risk for the subject and is calculated by subtracting the measured bone mineral density from a reference bone mineral density of a normal healthy adult in their thirties (YN=young normal), which reflects the approximate age of peak bone density. This number is then divided by the standard deviation (SD).

$$T\ \text{Score}=(BMD-YN)/SD$$

Under the WHO guidelines, a normal BMD is that which is >−1 standard deviation of the BMD of the young adult reference; low bone mass or osteopenia is a BMD of −1 to −2.5 standard deviations from BMD of the young adult reference. Osteoporosis is diagnosed where the BMD is <−2.5 standard deviations from the BMD of the young adult reference while severe osteoporosis is present where the BMD is <−2.5 standard deviations from the BMD of the young adult reference and the subject has had one or more osteoporotic fractures. Generally, a human subject's fracture risk appears to double for every standard deviation below the young adult reference range.

The Z score is the number of standard deviations the BMD value is above or below the age matched bone mineral density. The Z-score is not a diagnostic criterion for osteoporosis but can be useful in identifying those subjects warranting further assessment for long-term risk of osteoporosis and for testing of secondary causes of osteoporosis. A Z-score changes over time in relation to the T-score. A Z-score below −1.5 standard deviations indicates primary osteoporosis while a score of −1.5 standard deviations and higher indicates secondary osteoporosis. As is appreciated by those skilled in the art, the reference population determines the T and Z scores, and are thus subject to change as new reference populations are identified that provide a more consistent, predictive measure of osteoporosis and other degenerative bone disorders.

A number of techniques can be useful in assessing BMD. One widely used technique is dual x-ray absorbitiometry (DEXA). The x-ray beam in this technique has at least two distinct radiation energies that allow for measurement of two tissue types of differing density (e.g., bone and soft tissue). In some embodiments, the spine and the hip are imaged. A measurement of the hipbone density is informative and reliable because the hip is rarely affected by arthritic changes seen with age. The spine is imaged because loss of bone in osteoporosis is most pronounced in the trabecular bone that makes up the vertebrae. Measurements of total body bone mineral content and density are also possible with DEXA and can be useful for assessment of bone mineral accumulation during growth and development (e.g., peak BMD), and for body composition analysis.

Another method for assessing bone density is quantitative ultrasound, which measures the speed of sound reflected off the bone. Broadband ultrasonic attenuation (BUA) determines the density and the structure of the bone while the velocity of sound (VOS) across bone evaluates bone density and elasticity. Attenuation of the ultrasonic beam is based on the principle that the more complex the structure, the greater the attenuation of ultrasound. For example, the higher degree of connectivity of the trabeculae makes sound travel faster through the bone. Ultrasound measurements are generally used to assess peripheral bone but has high precision. Both the DEXA and ultrasound techniques can be used to assess apparent bone density calculated as bone mineral content per unit area ($g/cm^2$).

To determine bone density per bone volume, quantitative computed tomography (QCT) can be used. Density of a selected area on the CT image is compared to the densities of a set of known standards, such as a series of tubes filled with different concentrations of calcium solution imaged within the field of view of the CT. Because CT is capable of separately measuring the bone mineral density of the cortical bone and trabecular bone, on which structural strength typically depends, the QCT technique can be a better predictor of vertebral fracture risk.

In some embodiments, bone structure can be directly assessed by magnetic resonance imaging (MRI). Some types of degenerative bone disorders, such as male hypogonadism, lack large differences in bone mineral density of the vertebrae and hip, two types of bone imaged for measuring bone mineral density. High-resolution magnetic resonance imaging, including micro magnetic resonance imaging, permits the in vivo acquisition of images at resolutions high enough to discern individual trabeculae and ascertain the characteristics of bone microarchitecture. As such, this imaging technique allows quantitation of the factors affecting the integrity of the trabecular bone and identification of bone abnormalities not distinguishable based on other radiological or ultrasonic bone densitometry (Jiang et al., 2000, *J Musculoskelet Neuronal Interact.* 1(1):45-51). MRI images can be obtained by 3D-dimensional gradient-echo MR sequence with steady-state precession (Boutry et al., 2003, *Radiology* 227:708-717; Lin et al., 1998, *Osteoporos Int.* 8:16-24).

Other types of techniques that can be used to measure bone density include, as examples, single energy X-ray absorptiometry (SXA), which is generally used to measure the bone density in the wrist or heel; radiographic absorptiometry (RA), which uses an X-ray of the hand and a small metal wedge to calculate bone density; dual photon absorptiometry (DPA), which measures the spine, hip or total body; and single photon absorptiometry (SPA), which generally measures bone density in the wrist.

In addition to measurements of bone density, assays for biochemical markers can provide an indication of the state of bone remodeling. These markers can be used independently or as an adjunct to bone density measurements. As such, marker analysis can be pertinent where secondary osteoporosis is suspected. Some markers of bone formation are found in the serum while others are detectable in the urine. Exemplary markers in the serum include, among others, carboxy-terminal and amino-terminal propeptide of type 1 collagen, bone-specific alkaline phosphatase, and osteocalcin.

The carboxy-terminal and amino terminal peptides of collagen originate in the serum from cleavage of terminal portions of the type I collagen molecules in their procollagen form during collagen assembly. The serum concentration of these peptide products can be an indicator of bone formation. The peptides can be detected by immunoassays. However, these immunoassays do not distinguish between peptides generated from other collagen I sources, such as the skin. The marker bone-specific alkaline phosphatase is produced by osteoblasts and is essential for proper mineralization of the skeleton. Assays using antibodies with minimal cross-reactivity with alkaline phosphatase of other tissue origin (e.g., liver) can be a good indicator of bone formation (Hill et al., 1989, *Clin Chim Acta* 186:315-320). Another useful marker of bone formation in serum is osteocalcin, a small noncollagenous protein of osteoblastic origin that circulates in the serum in several forms. Osteocalcin is second in abundance to collagen in bone, and serum levels of the protein can reflect excess protein that is not incorporated into the bone matrix. Assays detecting either intact molecule or large amino-terminal fragment (residues 1-43) of osteocalcin can be reliable indicators of bone formation.

Markers of bone resorption are also detectable in the urine and/or serum. A significant class of bone resorption markers are products of collagen degradation, which include hydroxyproline, hydroxylysine, total and free pyridinoline (Pyd), and total and free deoxypyridinoline (Dpd); and N-telopeptide and C-telopeptide of collagen cross-links. Hydroxyproline and hydroxylysine are amino acids formed by the osteoblasts during the posttranslational processing of collagen. When bone is degraded, these amino acids are released into circulation, metabolized in the liver, and excreted in the urine. In addition to bone, other sources of hydroxyproline are the skin and dietary collagen. Consequently, accurate hydroxyproline measurements are made during a collagen-free diet. On the other hand, hydroxylysine measurements are not influenced by diet and can be measured without the need for special dietary regimens. Assays for hydroxyproline and hydroxylysine can use any accepted techniques, such as HPLC.

The biochemical markers pyridinoline (Pyd) and deoxypyridinoline (Dpd) also derive from the degradation of collagen, and originate from the cross-links that bridge collagen molecules and stabilize the collagen matrix. These crosslinks are derivatives of 3-hydroxypyridinium and form between hydroxylysine or lysine residues at the C- and N-terminal ends of one collagen molecule and the helical section of another collagen molecule. There are two main types of crosslinks; pyridinoline cross-links and deoxypyridinoline cross-links. The Pyd is more specific to bone but is not as abundant. Upon degradation of collagen, both types of cross-links enter the circulation as free or peptide bound forms and are excreted into the urine. Standard techniques for measuring these products include immunoassays and high-performance liquid chromatography (HLPC) (Seyedin et al., 1993,

*J Bone Miner Res* 8:635-42; Robins et al., 1994, *J Bone Miner Res* 9:1643-9; Pyrilinks-D, Metra Biosystems). The Pyd product is a sensitive marker of bone resorption and is a good indicator of metabolic bone diseases including, among others, osteoporosis, hyperparathyroidism, hyperthyroidism, and Paget's Disease.

The markers N-telopeptide (NTx) and C-telopetides (CTx) of type I collagen are simply the peptide forms containing the crosslinks discussed above as they are released into the circulation and into the urine following collagen degradation. As with the pyridinoline and deoxypyridinoline products, the N- telopeptide and C-telopeptide are detectable using HPLC or immunoassays (see, e.g., Gamero et al., 2001, *Clin Chem* 47:4-694-702; Rosenquist et al., 1998, Clin Chem 44:2281-9; Clemens et al., 1997, *Clin Chem* 43:2058-63). Immunoassays are available under the tradename Osteomark® for detecting NTx (Oxtex International and Wampole Laboratories, Princeton, N.J., USA) and under the tradename CrossLaps for detecting CTx (Osteometer Biotech, Copenhagen, Denmark; U.S. Pat. No. 6,107,047).

Other markers useful as indicators of bone resorption are tartrate-resistant acid phosphatase and bone sialoprotein. As presented in the descriptions herein, the tartrate resistant acid phosphatase (TRAP or TRACP) is an enzyme thought to participate in bone resorption. Three types of TRACP, isoform 5a, isoform 5b, and an isoform in osteoblasts, are known. TRACP 5b is present in osteoclasts and macrophages and appears to be released during bone resorption. Studies suggest that it plays a role in generating reactive oxygen species that fragment resorbed bone products within the osteoclast (Halleen et al., 1999, *J Biol Chem,* 274(22):907-10). The origin of TRACP 5a is less well known, but studies indicate its presence in macrophages and dendritic cells cultured in vitro and may be a marker for rheumatoid arthritis (Janckila et al., 2003, *J Bone Mineral Res* 18(10):1916). A third form of TRACP is present in osteoblasts but has not been well characterized. Studies implicate a possible role of the third isoform in fluoride-mediated osteogenesis (Lau et al., 2003, *J Bone Mineral Res* 18(10):1987).

Of the various TRACP isoforms, TRACP 5b appears to be a useful biochemical index for bone resorption based on its presence in osteoclasts and its release during bone resorption. Its increase in serum correlates with increased bone remodeling found in osteoporosis and renal osteodystrophy. TRACP 5b can be detected as part of total TRACP in serum determined by suitable techniques, such as immunoassays. Serum TRAPC 5b isoform, however, is also secreted as inactive and active forms. Osteoclasts secrete the active enzyme, which becomes inactivated in serum, while macrophages secrete the inactive enzyme. (Nakasato et al., 1999, *Clin Chem* 45:2150-7; Halleen et al., 2001, *Clin Chem* 47:597:-600). Assays that distinguish between the active and inactive enzymes are available to provide a more accurate assessment of TRACP 5b (see, e.g., BoneTRAP® assay, Suomen Bioanalytiikka, Finland).

In addition to the in vivo assays for assessing bone remodeling and resorption, various in vitro assays can be used to examine the effect of the compounds and combination treatments on osteoclast activity. An exemplary in vitro assay is the dentin resorption pit assay, various versions of which are described in the art (see, e.g., Tamura et al., 1993, *J Bone Miner Res* 8:953-960). Generally, osteoclasts are grown in suitable media (e.g., modified eagles media (MEM)), plated on dentin slices, and incubated on the dentin slices for additional time. After removal of cells by mechanical, chemical, and/or enzymatic treatment, resorption pits formed by osteoclast activity are examined by electron microscopy or staining with Mayer's hematoxylin. The resorbed area relative to the whole dentin surface area can provide a relative measure of the resorption rate.

In vitro analysis can also use differentiation markers expressed by osteoclasts and osteoblasts to examine the effect of Syk inhibitors and combination treatments on osteoclastogenesis and osteoblastogenesis. As noted above, an exemplary marker for osteoclastogenesis is expression of TRACP 5b. Other osteoclast differentiation markers will be apparent to the skilled artisan (e.g., vitronectin receptor, calcitonin receptor, cathepsin K, etc.; see Nomiyama et al., 2005, *J Interferon Cytokine Res.* 25(4):227-31). Exemplary osteoblast markers include osteoblast/osteocyte factor 45 (OF 45) (Peterson et al., 2000, *J Biol Chem.* 275(46):36172-80), bone-specific alkaline phosphatase, STRO-1, RANKL, and osteoprotegrin (Atkins et al., 2003, *J Bone Miner Res.* 18(6): 1088-98).

In some embodiments, animal models of osteoporosis can be used to determine efficacy and dosages for therapeutic purposes. One animal model is ovariectomized rats and mice, which develop osteoporosis similar to human osteoporosis. Osteoporosis and bone degeneration can also be induced in animals by glucocorticoid administration or by immobilizing the animal to limit mechanical stress on the bones.

In addition to experimentally induced systems, transgenic animal models mimicking various types of degenerative bone disorders can be used. One transgenic system for senile osteoporosis uses induced apoptosis of osteoblasts directed by fusing the promoter for osteocalcin gene to the herpes simplex thymidine kinase gene. Treatment of the transgenic animal with gangcyclovir leads to ablation of osteoblasts expressing the thymidine kinase (Corral et al., 1998, *Proc Natl Acad Sci USA* 95(23):13835-40). Another transgenic model employs overexpression of RANKL, either ubiquitously or restricted to the liver, to activate osteoclastogenesis and accelerate bone resorption (Mizuno et al., 2000, *J Bone Miner Metab.* 20(6):337-44). This transgenic animal shows a decrease in bone mineral density and an increase in bone fragility characteristic of osteoporosis in humans. Other types of animal models with genetic abnormalities analogous to those found in human subjects can be also used to determine the efficacy of Syk kinase inhibitors in treating degenerative bone disorders.

6.4 Compounds and Compositions for Treating Degenerative Bone Disorders

In reference to various Syk inhibitor compounds, the terms used to describe the compounds will have their ordinary and common meaning as used by those in the art unless a different definition is provided herein or is provided in the references describing the specific inhibitor compounds.

"Alkyl" by itself or as part of another substituent refers to a saturated or unsaturated, branched, straight-chain or cyclic monovalent hydrocarbon group having the stated number of carbon atoms (i.e., $C_1$-$C_6$ means from one to six carbon atoms) derived by the removal of one hydrogen atom from a single carbon atom of a parent alkane, alkene or alkyne. Alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups composed of from 1 to 6 carbon atoms. In some embodiments, the alkyl groups are (C1-C6) alkyl.

"Alkanyl" by itself or as part of another substituent refers to a saturated branched, straight-chain or cyclic alkyl group. Alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc. In some embodiments, the alkanyl groups are (C1-C6) alkanyl.

"Alkenyl" by itself or as part of another substituent refers to an unsaturated branched, straight-chain or cyclic alkyl group having at least one carbon-carbon double bond derived by the removal of one hydrogen atom from a single carbon atom of a parent alkene. The group can be in either the cis or trans conformation about the double bond(s). Alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl ; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc. In some embodiments, the alkenyl groups are (C2-C6) alkenyl.

"Alkynyl" by itself or as part of another substituent refers to an unsaturated branched, straight-chain or cyclic alkyl group having at least one carbon-carbon triple bond derived by the removal of one hydrogen atom from a single carbon atom of a parent alkyne. Alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl , etc. In some embodiments, the alkynyl groups are (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In some embodiments, the alkyldiyl group is (C1-C6) alkyldiyl. In some embodiments, the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkyleno group is (C1-C6) or (C1-C3) alkyleno. In some embodiments, the alkyleno groups are straight-chain saturated alkano groups, e.g., methano, ethano, propano, butano, and the like.

"Heteroalkyl," Heteroalkanyl," Heteroalkenyl," Heteroalkynyl," Heteroalkyldil" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Aryl" by itself or as part of another substituent refers to a monovalent aromatic hydrocarbon group having the stated number of carbon ring atoms (i.e., $C_5$-$C_{14}$ means from 5 to 14 carbon ring atoms) derived by the removal of one hydrogen atom from a single carbon atom of a parent aromatic ring system. Aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is ($C_5$-$C_{14}$) aryl or ($C_5$-$C_{10}$) aryl. In some embodiments, the aryls are cyclopentadienyl, phenyl, and napthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Arylaryl groups include, but are not limited to, biphenyl, triphenyl, phenyl-naphthyl, binaphthyl, biphenylnaphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. In some embodiments, each parent aromatic ring system of an arylaryl group is independently a (C5-C15) aromatic, more preferably a (C5-C10) aromatic. In some embodiments, the arylaryl groups are groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Biaryl groups include, but are not limited to, biphenyl, binaphthyl, bianthracyl, and the like. In some embodiments, the aromatic ring systems are (C5-C15) aromatic rings, more preferably (C5-C10) aromatic rings. In some embodiments, the biaryl group is biphenyl.

"Arylalkyl" by itself or as part of another substituent refers to an acyclic alkyl group in which one of the hydrogen atoms bonded to a carbon atom, typically a terminal or $sp_3$ carbon atom, is replaced with an aryl group. Arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophylethan-1-yl and the like. Where specific alkyl moieties are intended, the nomenclature arylalkanyl, arylalkenyl and/or arylalkynyl is used. In some embodiments, the arylalkyl group is ($C_6$-$C_{16}$) arylalkyl, e.g., the alkanyl, alkenyl or alkynyl moiety of the arylalkyl group is ($C_1$-$C_6$) and the aryl moiety is ($C_5$-$C_{10}$). In some embodiments, the arylalkyl group is ($C_6$-$C_{13}$), e.g., the alkanyl, alkenyl or alkynyl moiety of the arylalkyl group is ($C_1$-$C_3$) and the aryl moiety is ($C_5$-$C_{10}$).

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as various hydro isomers thereof.

"Parent Heteroaromatic Ring System" refers to a parent aromatic ring system in which one or more carbon atoms are each independently replaced with the same or different heteroatoms or heteroatomic groups. Heteroatoms or heteroatomic groups to replace the carbon atoms include, but are not limited to, N, NH, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Also included in the definition of "parent heteroaromatic ring system" are those recognized rings that include substituents, such as benzopyrone. Parent heteroaromatic ring systems include, but are not limited to, arsindole, benzodioxan, benzofuiran, benzopyrone, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (i.e., "5-14 membered" means from 5 to 14 ring atoms) derived by the removal of one hydrogen atom from a single atom of a parent heteroaromatic ring system. Heteroaryl groups include, but are not limited to, groups derived from acridine, arsindole, carbazole, .beta.-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl or a 5-10 membered heteroaryl.

"Heteroarylalkyl" by itself or as part of another substituent refers to an acyclic alkyl group in which one of the hydrogen atoms bonded to a carbon atom, such as a terminal or $sp_3$ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In some embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Substituted Alkyl, Aryl, Arylalkyl, Heteroaryl or Heteroarylakyl" refers to an alkyl, aryl, arylalkyl, heteroaryl or heteroarylakyl group in which one or more hydrogen atoms is replaced with another substituent group. Exemplary substituent groups include, but are not limited to, —OR', —SR', —NR'R', —NO$_2$, —NO, —CN, —CF$_3$, halogen (e.g., —F, —Cl , —Br and —I), —C(O)R', —C(O)OR', —C(O)NR', —S(O)$_2$R', —S(O)$_2$NR'R', where each R' is independently selected from the group consisting of hydrogen and (C$_1$-C$_6$) alkyl.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. In some embodiments, each parent heteroaromatic ring system is independently a 5-15 membered heteroaromatic, more preferably a 5-10 membered heteroaromatic. In some embodiments, heteroaryl-heteroaryl groups are those in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1 C2) haloalkyl" includes fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active drugs to yield prodrugs are well known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

Various compounds that inhibit Syk activity can be used in the methods described herein. These include, among others, small organic molecules, peptides or proteins, or nucleic acids. As used herein, a "Syk inhibitor" or "Syk kinase inhibitor" refers to any compound that directly inhibits the activity of Syk kinase itself or inhibits interaction with other cellular targets needed for proper Syk function, in the IC$_{50}$ range described herein. Inhibitors include the classical description of enzyme inhibitors, such as competitive, noncompetitive and uncompetitive inhibitors. Compounds that are "Syk inhibitors" are those that display an $IC_{50}$ with respect to a Syk kinase activity, such as the ability of Syk kinase to phosphorylate a synthetic or endogenous substrate, in an in vitro or cellular assay, in the range of about 5 uM or lower, about 1 uM or lower, about 500 nm or lower, about 100 nM or lower, about 50 nM or lower, about 100 nM or lower, or about 1 nM or lower. Skilled artisans will appreciate that compounds exhibiting lower $IC_{50}$s, such as in the range of about 100 nM, 10 nM, 1 nM, or even lower, are useful for the methods herein.

In some embodiments, the inhibitor compound can be selective for Syk kinase. A "Syk kinase selective inhibitory compound" refers to a compound displaying selectivity for Syk, which can be defined as the ratio of an $IC_{50}$ for a reference kinase over an $IC_{50}$ for Syk kinase in a defined set of assays. Generally, the Syk kinase selective inhibitory compound can have a selectivity for Syk kinase that is greater than about 10, greater than about 50, greater than about 100, greater than about 1000, or higher. The reference kinase can be any kinase activity, including kinases such as, by way of example and not limitation, Aurora-A, AKT, CDK1/cyclinB, CDK2/cyclinA, CDK3/cyclinE, CDK5/p35, CDK6/cyclinD3, CDK7/cyclinH/MAT1, CHK1, CHK2, EGFR, c-RAF, RAS, cSRC, Yes, Fyn, Lck, Fes, Lyn, Bmx, FGFR3, GSK3α, GSK3β, P13, IGF-1R, MAPK2, MAPKAP-K2, JNK, MEK1, p70S6K, PAK2, PDGFRα, PDGFRβ, PDK1, PKA, PKCE, PKC, PKD2, VEGF, PRAK, PRK2, ROCK-II, Rsk1, Rsk2, Rsk3, and SGK. Various assays for each of the kinases will be apparent to the skilled artisan. For example, assays for Aurora kinase activities can use natural or synthetic substrates (e.g., fluorescent peptides, Histone H3) in in vitro assays, or measurement of phosphorylated products in cells (Walter et al., 2000, *Oncogene* 19(42):4906-16). Kinase activities can be detected using various approaches, including, by way of example and not limitation, immunoprecipitation (e.g., Cyclex Aurora A kinase Assay; MBL Corp, Woburn, Mass., USA), mobility shift (e.g., Caliper Technologies, Mountain View, Calif., USA), autofluorescent fusion protein substrates (e.g., U.S. Pat. No. 6,248,550), and FRET based assays (Z-LYTE®; Invitrogen, Calif., USA).

Various Syk kinase inhibitors can be used in the methods herein, and is meant to include, where applicable, the salts, hydrates, solvates, and N-oxides of the corresponding inhibitor compounds. In some embodiments, the Syk kinase inhibitor comprises a 2,4-pyrimidinediamine compound and its various derivatives, for example, such as described in U.S. application Ser. No. 10/631,029; PCT publication No. WO 2004/014382, and other references described below, all of which are incorporated herein by reference in their entirety. These compounds generally comprise a 2,4-pyrimidinediamine "core" having the following structure and numbering convention:

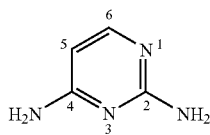

The compounds are substituted at the C2 nitrogen (N2) to form a secondary amine and are optionally further substituted at one or more of the following positions: the C4 nitrogen (N4), the C5 position and/or the C6 position. When substituted at N4, the substituent forms a secondary amine. The substituent at N2, as well as the optional substituents at the other positions, may range broadly in character and physicochemical properties. For example, the substituent(s) can be a branched, straight-chained or cyclic alkyl, a branched, straight-chained or cyclic heteroalkyl, a mono- or polycyclic aryl a mono- or polycyclic heteroaryl or combinations of these groups. These substituent groups can be further substituted as is described in, among others, U.S. application Ser. No. 10/355,543 (published at U.S. application publication No. 2004/0029902); U.S. application Ser. No. 10/631,029; and PCT publication WO 2004/014382.

The N2 and/or N4 substituents can be attached directly to their respective nitrogen atoms, or they can be spaced away from their respective nitrogen atoms via linkers, which can be the same or different. The nature of the linkers can vary widely, and can include virtually any combination of atoms or groups useful for spacing one molecular moiety from another. For example, the linker can be an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

The substituents at the N2, N4, C5 and/or C6 positions, as well as the optional linkers, can be further substituted with one or more of the same or different substituent groups. The nature of these substituent groups can vary broadly. Non-limiting examples of suitable substituent groups include branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities can be protected or unprotected, as is well-known in the art.

In some embodiments, the 2,4-pyrimidinediamine comprise compounds according to structural formula (I):

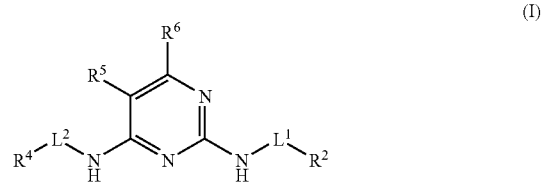

including salts, hydrates, solvates and N-oxides thereof, wherein:

$L^1$ and $L^2$ are each, independently of one another, selected from the group consisting of a direct bond and a linker;

$R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^4$ is selected from the group consisting of hydrogen, (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^5$ is selected from the group consisting of $R^6$, (C1-C6) alkyl optionally substituted with one or more of the same or different $R^8$ groups, (C1-C4) alkanyl optionally substituted with one or more of the same or different $R^8$ groups, (C2-C4) alkenyl optionally substituted with one or more of the same or different $R^8$ groups and (C2-C4) alkynyl optionally substituted with one or more of the same or different $R^8$ groups;

each $R^6$ is independently selected from the group consisting of hydrogen, an electronegative group, $-OR^d$, $-SR^d$, (C1-C3) haloalkyloxy, (C1-C3) perhaloalkyloxy, $-NR^cR^c$, halogen, (C1-C3)haloalkyl, (C1-C3) perhaloalkyl, $-CF_3$, $-CH_2CF_3$, $-CF_2CF_3$, $-CN$, $-NC$, $-OCN$, $-SCN$, $-NO$, $-NO_2$, $-N_3$, $-S(O)R^d$, $-S(O)_2R^d$, $-S(O)_2OR^d$, $-S(O)NR^cR^c$, $-S(O)_2NR^cR^c$, $-OS(O)R^d$, $-OS(O)_2R^d$, $-OS(O)_2OR^d$, $-OS(O)NR^cR^c$, $-OS(O)_2NR^cR^c$, $-C(O)R^d$, $-C(O)OR^d$, $-C(O)NR^cR^c$, $-C(NH)NR^cR^c$, $-OC(O)R^d$, $-SC(O)R^d$, $-OC(O)OR^d$, $-SC(O)OR^d$, $-OC(O)NR^cR^c$, $-SC(O)NR^cR^c$, $-OC(NH)NR^cR^c$, $-SC(NH)NR^cR^c$, $-[NHC(O)]_nR^d$, $-[NHC(O)]_nOR^d$, $-[NHC(O)]_nNR^cR^c$ and $-[NHC(NH)]_nNR^cR^c$, (C5-C10) aryl optionally substituted with one or more of the same or different $R^8$ groups, phenyl optionally substituted with one or more of the same or different $R^8$ groups, (C6-C16) arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;

$R^8$ is selected from the group consisting of $R^a$, $R^b$, $R^a$ substituted with one or more of the same or different $R^a$ or $R^b$, $-OR^a$ substituted with one or more of the same or different $R^a$ or $R^b$, $-B(OR^a)_2$, $-B(NR^cR^c)_2$, $-(CH_2)_m-R^b$, $-(CHR^a)_m-R^b$, $-O-(CH_2)_m-R^b$, $-S-(CH_2)_m-R^b$, $-O-CHR^aR^b$, $-O-CR^a(R^b)_2$, $-O-(CHR^a)_m-R^b$, $-O(CH_2)_m-CH[(CH_2)_mR^b]R^b$, $-S-(CHR^a)_m-R^b$, $-C(O)NH-(CH_2)_m-R^b$, $-C(O)NH-(CHR^a)_m-R^b$, $-O-(CH_2)_m-C(O)NH-(CH_2)_m-R^b$, $-S-(CH_2)_m-C(O)NH-(CH_2)_m-R^b$, $-O-(CHR^a)_m-C(O)NH-(CHR^a)_m-R^b$, $-S-(CHR^a)_m-C(O)NH-(CHR^a)_m-R^b$, $-NH-(CH_2)_m-R^b$, $-NH-(CHR^a)_m-R^b$, $-NH[(CH_2)_m R^b]$, $-N[(CH_2)_mR^b]_2$, $-NH-C(O)-NH-(CH_2)_m-R^b$, $-NH-C(O)-(CH_2)_m-CHR^bR^b$ and $-NH-(CH_2)_m-C(O)-NH-(CH_2)_m-R^b$;

each $R^a$ is independently selected from the group consisting of hydrogen, (C1—C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl; each $R^b$ is a suitable group independently selected from the group consisting of $=O$, $-OR^d$, (C1-C3) haloalkyloxy, $-OCF_3$, $=S$, $-SR^d$, $=NR^d$, $=NOR^d$, $-NR^cR^c$, halogen, $-CF_3$, $-CN$, $-NC$, $-OCN$, $-SCN$, $-NO$, $-NO_2$, $=N_2$, $-N_3$, $-S(O)R^d$, $-S(O)_2R^d$, $-S(O)_2OR^d$, $-S(O)NR^cR^c$, $-S(O)_2NR^cR^c$, $-OS(O)R^d$, $-OS(O)_2R^d$, $-OS(O)_2OR^d$, $-OS(O)_2NR^cR^c$, $-C(O)R^d$, $-C(O)OR^d$, $-C(O)NR^cR^c$, $-C(NH)NR^cR^c$, $-C(NR^a)NR^cR^c$, $-C(NOH)R^a$, $-C(NOH)NR^cR^c$, $-OC(O)R^d$, $-OC(O)OR^d$, $-OC(O)NR^cR^c$, $-OC(NH)NR^cR^c$, $-OC(NR^a)NR^cR^c$, $-[NHC(O)]_nR^d$, $-[NR^aC(O)]_nR^d$, $-[NHC(O)]_nOR^d$, $-[NR^aC(O)]_nOR^d$, $-[NHC(O)]_nNR^cR^c$, $-[NR^aC(O)]_nNR^cR^c$, $-[NHC(NH)]_nNR^cR^c$ and $-[NR^aC(NR^a)]_nNR^cR^c$;

each $R^c$ is independently $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which is optionally substituted with one or more of the same or different $R^a$ or suitable $R^b$ groups;

each $R^d$ is independently $R^a$;

each m is independently an integer from 1 to 3; and each n is independently an integer from 0 to 3.

In some embodiments, the 2,4-pyrimidinediamine compounds of structural formula (I) above comprise compounds in which $L^1$ and $L^2$ are each a direct bond;

$R^2$ is selected from the group consisting of phenyl mono substituted at the 3- or 5-position with an $R^8$ group, phenyl di- or tri-substituted with one or more of the same or different $R^8$ groups and 5-15 membered heteroaryl optionally substituted with one or more of the same or different $R^8$ groups;

$R^4$ is selected from the group consisting of phenyl substituted with one or more of the same or different $R^8$ groups and 5-15 membered heteroaryl optionally substituted with one or more of the same or different $R^8$ groups;

$R^5$ is selected from the group consisting of $-CN$, $-NC$, $-NO_2$, fluoro, (C1-C3) haloalkyl, (C1-C3) perhaloalkyl, (C1-C3) fluoroalkyl, (C1-C3) perfluoroalkyl, $-CF_3$, (C1-C3) haloalkoxy, (C1-C3) perhaloalkoxy, (C1-C3) fluoroalkoxy, (C1-C3) perfluoroalkoxy, $-OCF_3$, $-C(O)R^a$, $-C(O)OR^a$, $-C(O)CF_3$ and $-C(O)OCF_3$;

$R^6$ is hydrogen;

$R^8$ is selected from the group consisting of $R^e$, $R^b$, $R^e$ substituted with one or more of the same or different $R^a$ or $R^b$, $-OR^a$ substituted with one or more of the same or different $R^a$ or $R^b$, $-B(OR^a)_2$, $-B(N^cR^c)_2$, $-(CH_2)_m-R^b$, $-(CHR^a)_m-R^b$, $-O-(CH_2)_m-R^b$, $-S-(CH_2)_m-R^b$, $-O-CHR^aR^b$, $-O-CR^a(R^b)_2$, $-O-(CHR^a)_m-R^b$, $-O-(CH_2)_m-CH[(CH_2)_mR^b]R^b$, $-S-(CHR^a)_mR^b$, $-C(O)NH-(CH_2)_m-R^b$, $-C(O)NH-(CHR^a)_m-R^b$, $-O-(CH_2)_m-C(O)NH-(CH_2)_m-R^b$, $-S-(CH_2)_m-C(O)NH-(CH_2)_m-R^b$, $-O-(CHR^a)_m-C(O)NH-(CHR^a)_m-R^b$, $-S-(CHR^a)_m-C(O)NH-(CHR^a)_m-R^b$, $-NH-(CH_2)_m-R^b$, $-NH-(CHR^a)_m-R^b$, $-NH[(CH_2)_m R^b]$, $-N[(CH_2)_mR^b]_2$, $-NH-C(O)-NH-(CH_2)_m-R^b$, $-NH-C(O)-(CH_2)_m-CHR^bR^b$ and $-NH-(CH_2)_m-C(O)-NH-(CH_2)_m-R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, $S(O)_2OR^d$, $S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR_d$, —OC(O)$NR^cR^c$, —$OC(NH)NR^cR^c$, —$OC(NR^a)NR^cR^c$, —[NHC(O)]$_n$ $R^d$, —[$NR^aC(O)]_nR^d$, —[NHC(O)]$_n$$OR^d$, —[$NR^aC(O)]_n$ $OR^d$, —[NHC(O)]$_n$$NR^cR^c$, —[$NR^aC(O)]_n$$NR^cR^c$, —[NHC(NH)]$_n$$NR^cR^c$ and —[$NR^aC(NR^a)]_n$$NR^cR^c$;

each $R^c$ is independently a protecting group or $R^a$, or, alternatively, two $R^c$ are taken together with the nitrogen atom to which they are bonded to form a 5 to 8-membered cycloheteroalkyl or heteroaryl which may optionally include one or more of the same or different additional heteroatoms and which may optionally be substituted with one or more of the same or different $R^a$ groups;

each $R^d$ is independently a protecting group or $R^a$;

each $R^e$ is independently selected from the group consisting of (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each m is independently an integer from 1 to 3; and each n is independently an integer from 0 to 3, with the provisos that:

(1) when $R^2$ is a substituted phenyl, then $R^5$ is other than cyano; and (2) when $R^2$ and $R^4$ are each independently a substituted or unsubstituted pyrrole or indole, then the $R^2$ and $R^4$ are attached to the remainder of the molecule via a ring carbon atom.

Specific embodiments of Syk kinase inhibitory 2,4-pyrimidinediamine compounds are described in Appendixes A, B, C and D of U.S. provisional application Ser. No. 60/690,351, filed Jun. 13, 2005. These compounds useful in the methods described herein also include 2,4-pyrimidinediamine compounds described in U.S. application Ser. No. 10/355,543 (U.S. application publication No. 2004/0029902), including the exemplary 2,4-pyrimidinediamine compounds of Examples 7.3.1 to 7.3.1098, compounds of Example 7.3.1099; and compounds of Examples 7.3.1100 to 7.3.1165; U.S. application Ser. No. 10/631,029, filed Jul. 29, 2003, and corresponding PCT publication WO 2004/014382, including each of specific compounds disclosed as Examples 7.3.1 to 7.3.1165 and Examples 7.4.1 to 7.4.445; U.S. application Ser. Nos. 10/903,263 and 10/903,870, concurrently filed Jul. 30, 2004 (U.S. application publication No. 2005/0234049 and 2005/0209224, respectively), including each of specific compounds described in Table I (i.e., compound numbers 200 to 1358); and U.S. Application Ser. No. 60/630,808, filed Nov. 24, 2004. All publications and patent applications are incorporated herein by reference in their entirety.

In some embodiments, the Syk inhibitor compounds do not include specific embodiments described in Appendixes 1, 2, and 3 of U.S. provisional application No. 60/690,351, filed Jun. 13, 2005. These compounds are also described in U.S. provisional application No. 60/494,008, filed Aug. 7, 2003, and U.S. application Ser. No. 10/913,270 (U.S. application publication No. 2005/0113398), filed Aug. 6, 2004, including each of specific compounds disclosed in Tables 1-14 of application Ser. No. 10/913,270 (e.g., compound numbers 101-1164); and U.S. Application 60/572,534, filed May 18, 2004, and U.S. application Ser. No. 11/133,419, filed May 18, 2005, including each of specific compounds disclosed in Examples 7.10 to 7.14 and in Table 1 of application Ser. No. 11/133,419 (e.g., compound numbers 100-288). All patent applications and publications are incorporated herein by reference in their entirety.

An exemplary 2,4-pyrimidinediamine Syk inhibitor compound for use in the methods herein is N4-(2,2-dimethyl-3-oxo-4H-5-pyrid[1,4]oxazin-6-yl)-5-fluoro-N2-(3,4,5-trimethoxyphenyl)-2,4-pyrimidinediamine, denoted as compound 1007, as described in U.S. application Ser. Nos. 10/903,263 and 10/903,870.

As noted above, in some embodiments, the Syk inhibitory compounds can comprise prodrugs of the biologically active 2,4-pyrimidinediamine. In some embodiments, the Syk inhibitory compounds comprise prodrugs described in U.S. application Ser. No. 10/355,543 (U.S. application publication No. 2004/0029902); U.S. application Ser. No. 10/631,029, filed Jul. 29, 2003, and corresponding PCT publication WO2004/014382; and U.S. application Ser. No. 11/337,049 and international application PCT/US2006/001945, filed concurrently on Jan. 19, 2006, entitled "Prodrugs of 2,4-pyrimidinediamine compounds and their uses."

In some embodiments, the prodrugs include such active 2,4-pyrimidinediamine compounds in which one or more of the available primary or secondary amine groups is masked with a progroup $R^p$ that metabolizes in vivo to yield the active 2,4-pyrimidinediamine drug. The nature of the prodrug can vary, and will depend upon, among other factors, the desired water solubility of the prodrug, its intended mode of administration, and or its intended mechanism or site of metabolism to the active 2,4-pyrimidinediamine compound.

In some embodiments, the active 2,4-pyrimidinediamine compounds include pyrimidinediamines in which the N4-substituent of the 2,4-pyrimidine moiety is a substituted or unsubstituted nitrogen-containing heteroaryl ring of the formula

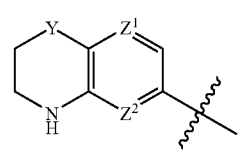

where $Z^1$ and $Z^2$ are each, independently of one another, selected from CH and N and Y is selected from $CH_2$, NH, O, S, S(O) and $S(O)_2$. Such prodrugs can include progroups $R^p$ at: one or both of the non-aromatic ring nitrogens of the heteroaryl ring, the N2-nitrogen of the 2,4-pyrimidinediamine moiety, the N4-nitrogen atom of the 2,4-pyrimidinediamine moiety and/or any available nitrogen atoms in the substituent attached to the N2 nitrogen atom of the 2,4-pyrimidinediamine moiety.

In some embodiments, the prodrugs of 2,4-pyrimidinediamines comprise compounds according to the following structural formula:

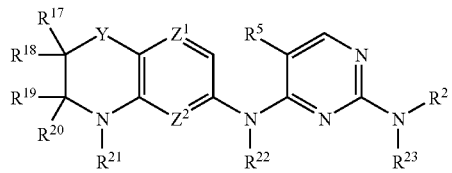

including salts, solvates, hydrates and N-oxides thereof, wherein:

Y is selected from $CH_2$, $NR^{24}$, O, S, S(O) and $S(O)_2$;

$Z^1$ and $Z^2$ are each, independently of one another, selected from CH and N;

$R^2$ is selected from lower alkyl optionally substituted with one or more of the same or different $R^8$ groups, lower cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C6-C14) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^5$ is selected from halo, fluoro, cyano, nitro, trihalomethyl and trifluoromethyl;

$R^8$ is selected from $R^a$, $R^b$, $R^a$ substituted with one or more, for example, from one to four, of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —$O$—$(CH_2)_m$—$R^b$, —$S$—$(CH_2)_m$—$R^b$, —$O$—$CHR^aR^b$, —$O$—$CR^a(R^b)_2$, —$O$—$(CHR^a)_m$—$R^b$, —$O$—$(CH_2)_m$—$CH[(CH_2)_mR^b]R^b$, —$S$—$(CHR^a)_m$—$R^b$, —$C(O)NH$—$(CH_2)_m$—$R^b$, —$C(O)NH$—$(CHR^a)_m$—$R^b$, —$O$—$(CH_2)_m$—$C(O)NH$—$(CH_2)_m$—$R^b$, —$S$—$(CH_2)_m$—$C(O)NH$—$(CH_2)_m$—$R^b$, —$O$—$(CHR^a)_m$—$C(O)NH$—$(CHR^a)_m$—$R^b$, —$S$—$(CHR^a)_m$—$C(O)NH$—$(CHR^a)_m$—$R^b$, —$NH$—$(CH_2)_m$—$R^b$, —$NH$—$(CHR^a)_m$—$R^b$, —$NH[(CH_2)_m\ R^b]$, —$N[(CH_2)_mR^b]_2$, —$NH$—$C(O)$—$NH$—$(CH_2)_m$—$R^b$, —$NH$—$C(O)$—$(CH_2)_m$—$CHR^bR^b$ and —$NH$—$(CH_2)_m$—$C(O)$—$NH$—$(CH_2)_m$—$R^b$;

$R^{17}$ is selected from hydrogen, halogen, fluoro, lower alkyl and methyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from hydrogen, halogen, fluoro, lower alkyl and methyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from hydrogen, lower alkyl, and methyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from hydrogen, lower alkyl and methyl or, alternatively, $R^{20}$ may be taken together with $R^{19}$ to form an oxo (=O) group or, together with the carbon atom to which they are attached, a spirocycle containing from 3 to 7 carbon atoms;

each $R^a$ is, independently of the others, selected from hydrogen, lower alkyl, lower cycloalkyl, cyclohexyl, (C4-C11) cycloalkylalkyl, (C6-C10) aryl, phenyl, (C7-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from =O, —$OR^a$, (C1-C3) haloalkyloxy, =S, —$SR^a$, =$NR^a$, =$NOR^a$, —$NR^cR^c$, halogen, —$CF_3$, —CN, —NC, —OCN, —SCN, —NO, —$NO_2$, =$N_2$, —$N_3$, —$S(O)R^a$, —$S(O)_2R^a$, —$S(O)_2OR^a$, —$S(O)NR^cR^c$, —$S(O)_2NR^cR^c$, —$OS(O)R^a$—$OS(O)_2R^a$, —$OS(O)_2OR^a$, —$OS(O)_2NR^cR^c$, —$C(O)R^a$, —$C(O)OR^a$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^a$, —$OC(O)OR^a$, —$OC(O)NR^cR^c$, —$OC(NH)NR^cR^c$, —$OC(NR^a)NR^cR^c$, —$[NHC(O)]_nR^a$, —$[NR^aC(O)]_nR^a$, —$[NHC(O)]_nOR^a$, —$[NR^aC(O)]_nOR^a$, —$[NHC(O)]_nNR^cR^c$, —$[NR^aC(O)]_nNR^cR^c$, —$[NHC(NH)]_nNR^cR^c$ and $[NR^aC(NR^a)]_nNR^cR^c$;

each $R^c$ is, independently of the others, selected from a protecting group and $R^a$, or, alternatively, the two $R^c$ bonded to the same nitrogen atom are taken together with that nitrogen atom to form a 5 to 8-membered cycloheteroalkyl or heteroaryl which may optionally include one or more of the same or different additional heteroatoms and which may optionally be substituted with one or more, for example, from one to four, of the same or different $R^a$ groups;

$R^{21}$, $R^{22}$ and $R^{23}$ are each, independently of one another, selected from hydrogen and a progroup $R^P$;

$R^{24}$ is selected from hydrogen, lower alkyl and progroup $R^P$;

each m is, independently of the others, an integer from 1 to 3; and each n is, independently of the others, an integer from 0 to 3, with the proviso that at least one of $R^{21}$, $R^{22}$, $R^{23}$ and $R^{24}$ is a progroup.

Exemplary prodrug compounds useful in the methods herein include specific compounds disclosed in Example 7.4 of U.S. application Ser. No. 10/355,543 (U.S. application publication No. 2004/0029902), each of specific compounds disclosed in Examples 7.4.1 to 7.4.445 of U.S. application Ser. No. 10/631,029, filed Jul. 29, 2003, and corresponding PCT publication WO2004/014382; and Examples 7.1, 7.2, 7.3, and 7.4 of U.S. application Ser. No. 11/337,049 and corresponding international application PCT/US2006/001945 discussed above.

In some embodiments, the kinase inhibitors can comprise compounds based on pyridine, pyrimidine, or triazine rings, as described in published U.S. application No. 2004/0106615 and PCT publication WO 2004/016597, which are incorporated herein by reference. Generally, the pyridine, pyrimidine, or triazine ring is directly attached to a 6-membered aryl or heteroaryl ring having 0-3 nitrogen atoms.

In some embodiments, the Syk kinase inhibitor can comprise compounds based on amino- or diaminotriazoles, as described in PCT publications WO 2005/013982 and WO 2004/046120, and published U.S. Application No. 20040214817, incorporated herein by reference. The aminotriazole compounds typically have substituents on the nitrogen atoms at the 3 or 4 position of the triazole ring, or the amino substituent on the ring. Exemplary aminotriazoles include, among others, aminotriazole pyridines and aminotriazole pyrimidines (see WO 2005/013982). Similarly, diaminotrazole compounds that inhibit kinases have substituents on one of the amino groups, and a substituent on the nitrogen atom at the 3 or 4 position of the triazole ring. Exemplary kinase inhibitors based on diaminotriazoles are described in WO2004/046120 and US 20040214817.

In other embodiments, the Syk kinase inhibitor can comprise compounds based on azaindoles., as described in U.S. Pat. No. 6,849,641, published U.S. Patent Application No. 2004/0053931, and PCT publication WO 03/000688, all of which are incorporated herein by reference. U.S. Pat. No. 6,849,641 describes 3-heteroarylideneazaindolin-2-one compounds. Similarly, U.S. Patent Application No. 2004/0053931 and PCT Publication No. WO 03/000688 describes azaindole compounds, among others, in which the pyrrolopyridine has aromatic or heterocyclic substituents (e.g., benzyl or indolyl) at the 2 or 3 position.

In other embodiments, the Syk kinase inhibitor can comprise compounds based on benzimidazoles, as described in published U.S. Patent Application No. 2004/0048868 and PCT publication WO 03/020698, both of which are incorporated herein by reference in their entirety. These compounds typically have substituents at the 1 and 2 positions of the imidazolyl along with additional subsitutions on the benzyl ring. Exemplary substituent at the 2 position is an aryl or heteroaryl, such as a pyrazolyl, triazolyl, imidazolyl, indolyl, indazolyl, thienopyrazolyl, tetrahydroindazolyl, tetrahydrocyclopentapyrazolyl, dihydrofuropyrazolyl, oxodihydropyridazinyl, tetrahydropyrrolopyrazolyl, oxotetrahydropyrrolopyrazolyl, tetrahydropyranopyrazolyl, tetrahydropyridinopyrazolyl, or oxodihydropyridinopyrazoly group.

In some embodiments, the Syk kinase inhibitor can comprise compounds based on thiazoles, as described in U.S. Pat. No. 6,762,179, published U.S. Patent Application Nos. 2003/0119856 and 2005/0004152, and PCT Publication No. WO 02/096905, which are incorporated herein by reference. Exemplary thiazole based inhibitors are 4-thiazolylpyrimidines in which the pyrimidine has substituents at the 2 and 4 positions. Typically, the group at the 2 position is a unsubstituted or substituted amine. Substituents on the amine are generally monocylic and heterocyclic rings, such as subsituted phenyl, indanyl, naphthyl, pyrimidinyl, or pyridyl rings.

In some embodiments, the Syk kinase inhibitor can comprise compounds based on pyrrolopyrimidines, as described in published U.S. Patent Application No. 2004/0142947 and PCT Publication Nos. WO 03/000695 and WO 2004/016597, which are incorporated herein by reference. In some embodiments, the pyrrolopyrimidine is attached to the 3 position of an indole ring. Generally, the indole has substituents on the 1 and/or 5 positions. An additional subsituent can be present at the 4 position of the pyrrolopyrimidine, including, among others, cyano, halo, hydroxy, nitro, aryl, heteroaryl, alkenyl, or alkynyl.

In further embodiments, the Syk kinase inhibitor can comprise compounds based on indazoles, as described in published U.S. Patent Application No. 2005/0009876 and U.S. Pat. No. 6,534,524, which are incorporated herein by reference in their entirety. U.S. Pat. No. 6,534,524 discloses inhibitor compounds in which the indazole has substituents at the 3 and/or 5 positions. Substituents at the 3 position are, among others, an unsubstituted aryl or substituted or unsubstituted heteroaryl, or CH=CH—R or CH=N—R, where R is a substituted or unsubstituted alkyl, alkelnyl, cycloalkyl, heterocycloalkyl, aryl or heteroaryl. Substituents at the 5 position are, among others, substituted or unsubstituted aryl, heteroaryl, or a Y-X, where Y is O, S, C=CH$_2$, C=O, S=O, SO$_2$, alkylidene, NH, N-alkyl, where R$^1$ is a substituted or an unsubstituted aryl, heteroaryl, or N—R', where R' is alkyl, cycloalkyl, heterocycloalkyl, aryl, heteroaryl, alkoxyl, or dialkylamide. Similarly, U.S. Patent Application No. 2005/0009876 discloses compounds in which the indazole has substituents at the 3 and/or 5 positions of the indazole. At the 3 position, a substituted or unsubstituted aryl, or a heteroaryl or heterocycle fused to a phenyl is attached via an alllkyl, such as an alkanyl, alkenyl, or alkynyl. Substituents at the 5 position are, among others, halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, substituted or unsubstituted heterocycloalkyl, ester, amide, cyano, or substituted or unsubstituted amine.

In some embodiments, the Syk kinase inhibitor can comprise bicyclic compounds, as described in U.S. Pat. No. 6,573,295, published U.S. Patent Application No. 2002/0062031, and PCT publication WO 00/27802, all which are incorporated herein by reference. In some of these embodiments, an unsubstituted or substituted benzyl is fused to a cycloalkyl, which is also substituted or unsubstituted. An exemplary cycloalkyl is a heptenyl. Exemplary bicyclic inhibitor compounds are {4-[2-(7-carbamoyl-8-cylohexyl-methoxy-2,3,4,5-tetrahydro-benzo[b]oxepin-(S)-5-ylcarbamoyl)-2-phenylacetylamino-ethyl]-2-phosphono-phenyl}-phosphonic acid; {4-[(S)-2-Acetylamino-2-(3-carbamoyl-2-cycycloxylmethoxy-6,7,8,9-tetrahydro-5H-benzocyclohepten-(S)-5-ylcarbamoyl)-ethyl]-phenoxy}-acetic acid; and (4-[(s)-2-Acetylamino-2-(3-carbamoyl-2-cycycloxylmethoxy-6,7,8,9-tetrahydro-5H-benzocyclohepten-(S)-5-ylcarbamoyl)-ethyl]-2-carboxymethyl-phenoxy-acetic acid.

In some embodiments, the kinase inhibitors can comprise chromenone oxime compounds as described in published U.S. Patent Application No. 2004/0198750 and PCT publication WO 2004/092154, which are incorporated herein by reference. Generally, substituents are on the 2 and 7 positions of the chromenone oxime nucleus.

Other kinase inhibitors compounds can include, substituted heterocycles (e.g., thiazole, oxazole, isoxazole, diazole, oxadiazole, dioxazole, furan, and pyridine) described in PCT publication WO99/47529, and substituted aryl or 5- or 6-membered heteraryl rings as described in PCT publication No. WO 2004/085388; and sulfonamides as described in Lai et al., 2003, *Bioorg Med Chem Lett.*, 13(18):3111-4. Other kinase inhibitor compounds will be apparent to the skilled artisan, and can be tested for Syk kinase inhibitory activity and effect on bone metabolism using the guidance provided herein.

Compounds can be tested in various biochemical and cellular assays for their inhibitory effect on Syk kinase. Syk kinase phosphorylates LAT and PLC-γ1, which leads to, among other things, degranulation in mast and/or basophil cells. Syk kinase activity is also observed in response to T-cell receptor stimulation. It is to be understood that any of these activities may be used to confirm the activity of the Syk inhibitor compounds. In some embodiments, the Syk kinase assay is a degranulation assay based on measurement of granule content release following stimulation with anti-IgE. These assays include, for example, measurement of tryptase, histamine, leukotriene LTC4, or hexosaminidase release. In other embodiments, the activity is determined by contacting an isolated Syk kinase, or an active fragment thereof with an inhibitor compound in the presence of a Syk kinase substrate (e.g., a synthetic peptide or a protein that is known to be phophorylated by Syk in a signaling cascade) and assessing whether the Syk kinase phosphorylates the substrate. Alternatively, the assay may be carried out with cells that express a Syk kinase. The cells can express the Syk kinase endogenously or they can be engineered to express a recombinant Syk kinase. The cells may optionally also express the Syk kinase substrate. Cells suitable for performing such confirmation assays, as well as methods of engineering suitable cells will be apparent to those of skill in the art. Suitable Syk kinase substrate include, by way of example and not limitation, human band 3 protein (Wang et al., 1999, *J Biol Chem.* 274(45), 32159-32166); protein kinase C (Kawakami et al., 2003, *Proc Natl Acad Sci USA,* 100(16):9470-5), tubulin (Peters et al., 1996, *J. Biol. Chem.* 271:4755), cortactin (Maruyama et al., 1996, *J. Biol. Chem.* 271:6631), and p50/ HS1 (Ruzzene et al., 1996, *Biochemistry* 35:1527). Specific examples of biochemical and cellular assays suitable for confirming the activity of the Syk inhibitor compounds are described in Fox et al., 1998, *Protein Science,* 7:2249, U.S. application Ser. No. 10/631,029, WO 2004/014382, and references cited therein, all of which are incorporated herein by reference.

6.5 Adjunctive Therapy for Treating Degenerative Bone Disorders and Preventing Loss of Bone Mass In the methods of treatment described herein, the Syk inhibitory compounds can be used independently or in combination with bone modulating agents that attenuate/inhibit bone resorption (i.e., antiresorptive agents) or promote bone formation (i.e., osteo-anabolic agents). In some embodiments, the combinations can be in the form of compositions comprising a Syk inhibitory compound and one or more compatible antiresorptive or osteo-anabolic agent. In some embodiments, the compositions can be a Syk inhibitory compound in combination with one or more compatible antiresorptive and osteoanabolic agents. In other embodiments, the combination can comprise adjunctive administration of the bone modulating agent with the Syk inhibitory compound, either simultaneously or sequentially. When the administration is sequential, the time period between administration of Syk inhibitor and bone modulating agent can be short (e.g., minutes to hrs) or long (e.g., days, weeks, months). In addition, where the degenerative bone disorder is secondary osteoporosis, the Syk inhibitors can also be used in compatible combinations with compounds typically used to treat the underlying disease or condition.

In accordance with the above, in some embodiments, the agents used adjunctively with the Syk inhibitors comprise anti-resorptive agents that inhibit or attenuate resorption of bone. Various antiresorptive agents are described in U.S. Pat. Nos. 6,835,722 and 6,284,730. A commonly used antiresorptive agents is 1,25-dihydroxyvitamin D3 (also known as calcitriol or 1,25-dihydroxycholecalciferol) and suitable analogs of calcitriol. As is known in the art, vitamin D is a family of steroid molecules involved in regulating calcium and phosphorous homeostasis. Generally, vitamin D3 (cholecalciferol) is formed through the action of ultraviolet light on 7-dehydrocholesterol. Within the liver, cholecalciferol is hydroxylated to 25-hydroxylcholecalciferol and then converted to 1,25-dihydroxylcholecalciferol by an enzyme present mainly in the kidneys. 1,25-dihydroxylcholecalciferol regulates the expression of proteins involved in transport of calcium from the lumen of the intestine and across the epithelial cells. About 800 IU of dietary form of vitamin D/per day is considered sufficient intake but tests of serum and urinary vitamin D and calcium can more accurately determine the necessary amount. Because hypercalcemia is a problem associated with 1,25-dihydroxycholecalciferol administration and certain other vitamin D analogs, vitamin D compounds that do not produce hypercalcemia is advantageous when vitamin D therapy is used adjunctively with Syk inhibitory compounds. Suitable analogs that do not cause significant hypercalcemia include, by way of example and not limitation, 1,25-dihydroxy-19-norvitamin D2, 1α-hydroxyvitamin D2, 1α-hydroxyvitamin D3, 1,25-dihydroxy-22-oxavitamin D3 (oxacalcitril), 1,25-dihydroxy-26,26,26,27, 27,27-hexfluorovitamin D3 (falecalcitriol); and 1,25-dihydroxydihydrotachysterol. Other suitable vitamin D analogs are described in U.S. Pat. Nos. 6,242,434; 5,532,228; 5,446,035; 5,206,229; 5,292,728; 5,194,431; and 4,866,048. All publications incorporated herein by reference.

In some embodiments, the antiresorptive agents can be polyphosphonates that inhibit bone resorption. A commonly used polyphosphonates are bisphosphonates, which are pyrophosphate analogues where the oxygen bridge has been replaced by a carbon with various substitutions. Bisphosphonate compounds bind to hydroxyapatite in the bone and is resistant to enzymatic hydrolysis. However, the exact mechanism of action is unclear and may function in a variety of ways, including (1) inhibition of osteoclast recruitment to the bone surface; (2) inhibition of osteoclast activity on the bone surface; (3) shortening of the osteoclast life span; and (4) alteration of the bone or bone mineral to reduce its rate of dissolution. Various bisphosphonates can be used adjunctively with the Syk inhibitory compounds, including, by way of example and not limitation, alendronate; risedronate; etidronate; tiludronate available under the tradename Skelid®; pamidronate; ibandronate; clodronate, and zoledronate, available under the tradename Zometa®.

Alendronate, available under the tradename Fosamax®, increases BMD in the spine, femoral neck and greater trochanter area, and decreases the risk of vertebral and non-vertebral fractures when administered at 10 mg/day in postmenopausal women, even if they already had vertebral fracture or are older than 75. Alendronate is generally used for osteoporosis treatment and prevention. In some embodiments, alendronate can be administered in once weekly dosing schedule for treatment and prevention of osteoporosis and for treatment of steroid induced osteoporosis. Risedronate, available under the tradename Actonel®, is effective in preventing bone loss caused by corticosteroids and in postmenopausal females with normal bone density. Risedronate increases spinal and hip density and prevents vertebrae and hip fractures. Etidronate, available under the tradename Didronel®, is given cyclically and has demonstrated effectiveness in treating vertebral osteoporosis and reducing vertebral fractures in postmenopausal women, and reducing bone loss in patients taking glucocorticoids. Pamidronate, available under the tradename Aredia®, is used to treat Paget's Disease, postmenopausal and corticosteroid-induced osteoporosis, and for prevention of postmenopausal osteoporosis. Standard dosages for various bisphosphonates and other compounds disclosed herein can be found in standard references, such as the *Physicians Desk Reference,* 59th Ed., Thomson PDR (2005), incorporated herein by reference.

In some embodiments, the antiresorptive agent can be calcitonin and various derivatives thereof. Calcitonin is a peptide of about 32 amino acids characterized by its hypocalcemic effect and its ability to inhibit bone resorption. Calcitonin as used herein is intended to cover naturally occurring forms, as well as variants and analogs, including peptide fragments, displaying the biological activity of the naturally occurring forms. Amino acid sequences for various forms of calcitonin include: human (gi|223389|prf||0802187A[223389]), salmon, (gi|345282|emb|CAA00272.1|[345282]); rat (Amar et al., 1980, *Proc Natl Acad Sci USA* 77 (8):4444-8), pig (gi|226251|prf||1503150A[226251]); and chicken (Lasmoles et al., 1985, *EMBO J.* 4(10):2603-7). Calcitonin variants, analogs, and formulations are described in Azria, M., *The Calcitonins. Physiology and Pharmacology*, Karger, Basal (1989); Siligardi et al., *Eur. J. Biochem.* 221:1117-1125 (1994); Epand et al., *Biochem Biophys Res Commun* 152: 203-207 (1988); and U.S. Pat. Nos. 6,617,423, 6,562,946, 5,977,298, 5,831,000, 5,428,129, 5,310,727, and 4,845,080, and 4,604,238 (all publications incorporated herein by reference). Calcitonin from difference species show wide variations in biological effect, with calcitonin from ultimobranchial glands of lower vertebrates having the highest potencies while the human form shows a somewhat lower potency. Consequently, an exemplary calcitonin form applied therapeutically is salmon calcitonin. Calcitonin is available in injection form, for subcutaneous or intramuscular administration, and as an intranasal spray (e.g., salmon calcitonin in spray form, available under the tradename Miacalcin®). Calcitonin treatments (e.g., 50-10 IU daily or every other day) have been shown to increase bone mineral density in the spine and reduce vertebral fractures.

In some embodiments, where the degenerative bone disorder is correlated with estrogen deficiency, estrogen or other compounds that modulate estrogen receptor activity can be administered adjunctively with the Syk inhibitor compounds. Hormone replacement therapy (HRT) with estrogen compounds is a standard care for the prevention and treatment of postmenopausal osteoporosis. As noted in the discussions above, estrogen deficiency increases osteoclast recruitment, and upregulates cellular factors, such as IL-1, IL-6, TNF-α, and RANKL, responsible for inducing osteoclastogenesis and octeoclast activity. Estrogen therapy can be used in conjunction with Syk inhibitors to decrease osteoclastogenesis and osteoclast activity associated with estrogen deficiency. Generally, estrogen supplements can be given at the level required to prevent bone loss. However, use of the Syk kinase inhibitors can allow administration of lower doses of estrogen, and thereby reduce the undesirable side effects of long term estrogen use. Typical forms of estrogen replacements include 17β-estradiol, conjugated equine estrogen (CEE) (available under the tradename Premarin®), and C-21 progestins, such as medroxyprogesterone acetate. Other estrogen compounds will be apparent to the skilled artisan.

In other embodiments, the estrogen deficiency can be treated with a selective estrogen receptor modulator (SERM). Various SERM compounds are known, and can act as estrogen receptor antagonists and agonists depending on the tissue. Suitable SERMs for use as adjunctive therapy include, by way of example and not limitation, raloxifene, tamoxifen, tibolone, ospemifene, lasofoxifene, and arzoxifene. An exemplary SERM for use with the present methods is raloxifene, a tissue-selective receptor agonist that has both estrogen agonist and antagonist properties. Raloxifene has estrogen-like activity on estrogen receptor in bone and cardiovascular tissue, but not in endometrium and breast. Thus, raloxifene preserves bone density and decreases serum total cholesterol level but does not display the unwanted side effects of endometrial hyperplasia and breast tissue hyperplasia.

In addition to antiresorptive agents, the adjunctively administered agent may comprise an osteo-anabolic agent that promotes bone formation. Thus, as used herein, osteo-anabolic agents refers to agents that promote osteoblastogenesis and/or activate osteoblast activity to increase bone formation. Some anabolic agents increase bone remodeling by activating both osteoclast and osteoblast activity but with the net effect of inducing more bone formation than resorption.

Accordingly, in some embodiments, the bone anabolic agent can be parathyroid hormone and various analogs thereof. Human parathyroid hormone is an 84 amino acid peptide secreted by the parathyroid cell in response to decrease in calcium levels, which is detected by calcium sensing receptors on the parathyroid cell membrane. PTH acts directly to increase renal tubular calcium resorption, and acts indirectly to increase intestinal calcium absorption by increase circulating levels of calcitriol through stimulation of renal 1-α choleacalciferol hydroxylase activity. In contrast to other types of antiresorptive agents, which reduce the rate of bone remodeling, PHT stimulates bone formation by osteoblasts, thereby increasing the rate of remodeling and the amount of bone formed in each cycle of remodeling. Intermittent administration of PTH appears to promote the anabolic properties of the hormone (see, e.g., U.S. Pat. No. 6,284, 730, incorporated herein by reference). The sequence of naturally occurring human parathyroid hormone is available at NCBI GenBank database at accession number gi|131547|sp|P01270|PTHY_HUMAN[131547].

As used herein, parathyroid hormone includes full length protein produced naturally, synthetically, or recombinantly, as well as variants and synthetic analogs, including fragments of PTH, that have bone inducing activity displayed by the full length peptide. Thus, useful fragments of PTH contain at least the amino acid residues required for bone inducing biological activity. Much of the activity of parathyroid hormone resides in the N-terminal sequence containing amino acid residues 1-34, also referred to as teriparatide, but bone anabolic activity is maintained in a peptide containing only amino acid residues 1-31. Teriparatide has demonstrated therapeutic effectiveness in countering postmenopausal osteoporosis by increasing trabecular bone thickness and connectivity (Neer et al., 2001, *N. Engl. J. Med.* 344: 1434-1441; Dempster et al., 2001, *J Bone Miner. Res.* 16:1846-1853; Jiang et al., 2003, *J. Bone Miner. Res.* 18:1932-1941). Other exemplary fragments of PTH with bone inducing activity include PTH peptides with amino acid residues 1-36, 1-37 and 1-38. Various synthetic analogs of parathyroid hormone are also given at Genbank accession numbers gi|21694083|emb|CAA00791.1| [21694083];

gi|2169408|emb|CAA00790.1[21694081];

gi|565142|gb|AAB31748.1||bbm|344998|bbs|151318 [565142];

gi|413488|emb|CAA00792.1|[413488]; and gi|413485|emb|CAA00789.1|[413485]. As will be apparent to the skilled artisan, PTH treatment is contraindicated for certain metabolic bone diseases characterized by elevated PTH levels, including primary and secondary hyperparathyroidism and renal osteodystrophy.

In some embodiments, the osteo-anabolic agent can be an androgen. As used herein, an androgen refers to a steroid hormone, such as testosterone or androsterone, that affects the development and maintenance of masculine characteristics. As discussed above, testosterone replacement therapy in hypogonadal males has been shown to increase bone mass density. Although it can be used to treat osteoporotic women, androgens have the undesirable property of masculinizing effects on the female patient. Consequently, treatments for osteoporosis using androgens are generally directed to males. Androgens include various forms of testosterone (Andro®, Andryl®, Delatest®, Depotest®, Duratest®, Everone®, Histerone®, Tesanone®, Testex®, Testrin®P.A.) and 17-α methyl testosterone (Android®, Metandren®, Oreton® Methyl, Virilon®). Other types of androgens include nandrolone decanoate (e.g., Andralone®, Duraboline®, Hybolin™ Improved, Neo-Durabolic), norethisterone acetate, fluoxymesterone (Halotestin®), and various derivatives thereof.

In some embodiments, the osteo-anabolic agent can be vitamin K2, known in various forms as menaquinone-7 or menatetrenone. Vitamin K2 is a cofactor of γ-carboxylase, which is involved in carboxylation of osteocalcin. Evidence suggests that vitamin K2 enhances osteocalcin accumulation and/or activity in the extracellular matrix and regulateS growth of hydroxyapatite crystals during bone mineralization (Mawatari et al., 2000, *J Bone Miner Res* 15(9): 1810-7). Administration of vitamin K2 produces a decrease in fracture occurrence and appears to maintain bone mineral density (Shiraki et al., 2000, *J Bone Miner Res* 15(3):515-21).

In some embodiments, the osteo-anabolic agent can be fluoride. Sodium fluoride markedly stimulates bone formation and increases axial bone mineral density. Low doses of fluoride reduce the risk of fractures and increase bone density. (Pak et al., 1995, *Ann Inter Med* 123:401-408). Various salts and formulations of fluoride may be used in the adjunctive treatments. Slow release formulations of NaF are described in Pak et al., 1996, *J Bone Miner Res.* 5:561-564. Recommended dosage is 25 mg twice daily, and generally in conjunction with supplementation with dietary calcium. Another form of fluoride shown to have osteo-anabolic activity is monofluorophosphate, as described in Ringe et al., 1999, *Osteop Int.* 9:171-178. Recommended dosage of monofluorophospate formulations is generally 20 mg of equivalent fluoride per day. Other effective doses can be determined by those skilled in the art. Combination treatments with fluoride and hormone replacement therapy (e.g., 17β-estradiol) can be used to produce positive effects on bone density in postemenopausal women (Alexandersen et al., 2001, *J. Clin. Endocrinol. Metab.* 86(3): 957-964).

In some embodiments, the osteo-anabolic agent can be strontium, a trace element related to calcium. Strontium in the form of strontium ranelate, which is renelic acid bound to two atoms of strontium and available under the tradename Protelos®, appears to stimulate osteoblast mediated bone formation and inhibit osteoclast mediated bone resorption. In vitro, strontium ranelate stimulates human cartilage matrix formation (Henrotin et al., 2001, *J Bone Miner Res.* 16(2):299-308). Strontium ranelate given at a dose of 1 gm to 2 gm per day decreases biochemical markers of bone resorption, increases the markers of bone formation, increases bone mineral density, and reduces the relative risk of vertebral fractures (Meunier et al., *J Clin Endocrinol Metab.* 87(5):2060-6; Reginster, J. Y, 2002, *Curr Pharm Des.* 8(21):1907-16.). Other forms of strontium compounds suitable as osteo-anabolic agents are described in Takahashi et al., 2002, *J Bone Miner Res* 18(6): 1082.

In some embodiments, the osteo-anabolic agent can be growth hormone (GH), including various derivatives and fragments that display the bone inducing biological activity of the naturally occurring forms. Human growth hormone (hGH) is a single polypeptide chain of 191 amino acids having two disulfide bonds, one between Cys-53 and Cys-165 forming a large loop in the molecule, and the other between Cys-182 and Cys-189 forming a small loop near the C-terminus (Roskam et al., 1979, *Nucleic Acids Res.* 7(2):305-20; DeNoto et al., 1981, *Nucleic Acids Res.* 9(15):3719-30). Alternative forms of hGH are known, including naturally occurring derivatives and engineered variants of hGH produced by recombinant methods. Any form of hGH that displays the osteogenic activity of native full length of hGH can be used. Truncated forms of hGH have been produced, either through the actions of enzymes or by recombinant methods. Fragments of hGH include 2-CAP, which has the first eight residues at the N-terminus of hGH removed by controlled treatment with trypsin. Exemplary formulations, including natural and synthetic forms of hGH, are described in U.S. Pat. No. 6,136,563; 6,022,711; 5,849,535; 5,763,394; 5,654,010; 5,633,352; 5,424,199; and 5,096,885. All references incorporated by reference.

In some embodiments, the osteo-anabolic agent can be insulin like growth factor (IGH-I). IGH-I promotes chondrocyte and osteoblast differentiation and growth. As with hGH, a decrease in IGH-I levels is suspected as a causative factor in osteoporosis. Administration of high doses of recombinant human IGH-I (e.g., 60 ug/kg/day) stimulates bone remodeling, as indicated by an increase in markers for bone resorption and bone formation, while lower doses (e.g., 15 mg/kg/day) increases markers osteocalcin and type I procollagen carboxy terminal peptide without increasing pyridinoline levels (Ghiron et al., 1995, *J Bone Miner Res* 10:1844-1852). Thus, lower doses appear to bias bone formation over bone resorption. Long-term administration shows positive effects by decreasing bone loss in osteoporotic females.

In some embodiments, the Syk inhibitory compounds can be administered in combination with supplemental dietary calcium, without or with any one or combination of the additional therapeutic agents discussed above. Forms of calcium readily absorbable in the intestine are useful as adjunctive therapies. These include calcium carbonate and calcium chelates, such as calcium citrate, calcium citrate malate, calcium lactate, calcium gluconate, calcium aspartate, and calcium orotate. As noted above, a set of recommendations for various age groups is provided in *National Institutes of Health Consensus Development Conference, Optimal Calcium Intake*, NIH Consensus Statement Online 1994 Jun. 6-8;,12(4):1-31. An exemplary recommended average intake for a healthy adult is about 1,000 to about 1,500 milligrams of calcium per day.

6.6 Pharmaceutical Compositions and Administration

When used to treat degenerative bone disorders or prevent bone loss, the Syk inhibitor compounds can be administered singly, as mixtures of one or more active compounds or as a mixture or combination with other agents useful for treating such diseases and/or symptoms associated with such diseases. The active compounds can be administered per se or as pharmaceutical compositions.

Pharmaceutical compositions comprising the active compounds of the invention can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the active compounds into preparations which can be used pharmaceutically. The actual pharmaceutical composition administered will depend upon the mode of administration. Virtually any mode of administration can be used, including, for example, topical, oral, systemic, inhalation, injection, transdermal, etc.

The active compound can be formulated in the pharmaceutical compositions per se, or in the form of a pharmaceutically acceptable salt. As used herein, the expression "pharmaceutically acceptable salt" means those salts which retain substantially the biological effectiveness and properties of the active compound and which is not biologically or otherwise undesirable. Such salts can be prepared from inorganic and organic acids and bases, as is well-known in the art. Typically, such salts are more soluble in aqueous solutions than the corresponding free acids and bases.

For topical administration, the active compound(s) can be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral, or pulmonary administration.

Useful injectable preparations include sterile suspensions, solutions or emulsions of the active compound(s) in aqueous or oily vehicles. The compositions can also contain formulating agents, such as suspending, stabilizing and/or dispersing agent. The formulations for injection can be presented in unit dosage form, e.g., in ampules or in multidose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration can be suitably formulated to give controlled release of the active compound.

For buccal administration, the compositions can take the form of tablets or lozenges formulated in conventional manner.

For rectal and vaginal routes of administration, the active compound(s) can be formulated as solutions (for retention enemas), suppositories, or ointments containing conventional suppository bases such as cocoa butter or other glycerides.

For administration by inhalation, the active compound(s) can be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g. gelatin, for use in an inhaler or insufflator can be formulated containing a powder mix of the compound and a suitable powder base such as lactose or starch.

For prolonged delivery, the active compound(s) can be formulated as a depot preparation, for administration by implantation; e.g., subcutaneous, intradermal, or intramuscular injection. Thus, for example, the active ingredient can be formulated with suitable polymeric or hydrophobic materials (e.g., as an emulsion in an acceptable oil) or ion exchange resins, or as sparingly soluble derivatives; e.g., as a sparingly soluble salt.

Alternatively, transdermal delivery systems can be used, manufactured as an adhesive disc or patch which slowly releases the active compound(s) for percutaneous absorption. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems can be employed. Liposomes and emulsions are well-known examples of delivery vehicles that can be used to deliver active compounds(s). Certain organic solvents such as dimethylsulfoxide (DMSO) can also be employed, although usually at the cost of greater toxicity.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

6.7 Effective Dosages

The active compound(s), or compositions thereof, will generally be used in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying degenerative bone disorder being treated and/or eradication or amelioration of one or more of the symptoms associated with the underlying disorder such that the patient reports an improvement in condition, notwithstanding that the patient may still be afflicted with the underlying disorder. Therapeutic benefit also includes halting or slowing the progression of the disease, regardless of whether improvement is realized. For prophylactic administration, the active compound can be administered to a patient at risk of developing a disorder characterized by, caused by or associated with bone loss and/or compromised bone integrity.

The amount of inhibitor compound(s) administered will depend upon a variety of factors, including, for example, the particular indication being treated, the mode of administration, whether the desired benefit is prophylactic o therapeutic, the severity of the indication being treated and the age and weight of the patient, the bioavailability of the particular active compound, etc. Determination of an effective dosage is well within the capabilities of those skilled in the art.

Initial dosages can be estimated initially from in vitro assays. For example, an initial dosage for use in animals can be formulated to achieve a circulating blood or serum concentration of compound that inhibits Syk sufficient to inhibit osteoclast activity in a dentin pit assay. Alternatively, an initial dosage for use in animals can be formulated to achieve a circulating blood or serum concentration of active compound that is equal to or greater than the $IC_{50}$ as measured in Syk kinase inhibition assay. Calculating dosages to achieve such circulating blood or serum concentrations taking into account the bioavailability of the particular inhibitor compound is well within the capabilities of skilled artisans. For guidance, the reader is referred to Fingl and Woodbury, "General Principles," In: *The Pharmaceutical Basis of Therapeutics*, Chapter 1, pp. 1-46, 1975, and the references cited therein.

Initial dosages can also be estimated from in vivo data, such as in the animal models described above. Dosage amounts will typically be in the range of from about 1 mg/kg/day to about 100 mg/kg/day, 200 mg/kg/day, 300 mg/kg/day, 400 mg/kg/day or 500 mg/kg/day, but can be higher or lower, depending upon, among other factors, the activity of the inhibitory compound, its bioavailability, the mode of administration and various factors discussed above. Dosage amount and interval can be adjusted individually to provide plasma levels of the active compound(s) which are sufficient to maintain therapeutic or prophylactic effect. In cases of local administration or selective uptake, such as local topical administration, the effective local concentration of active compound(s) can not be related to plasma concentration. Skilled artisans will be able to optimize effective dosages without undue experimentation.

The compound(s) can be administered once per day, a few or several times per day, or even multiple times per day, depending upon, among other things, the indication being treated and the judgment of the prescribing physician.

Preferably, the active compound(s) will provide therapeutic or prophylactic benefit without causing substantial toxicity. Toxicity of the active compound(s) can be determined using standard pharmaceutical procedures. The dose ratio between toxic and therapeutic (or prophylactic) effect is the therapeutic index. Active compound(s) that exhibit high therapeutic indices are preferred.

6.8 Kits

For administration of the compounds and treatment of degenerative bone disorders and to prevent bone loss, the Syk inhibitory compounds, antiresorptive agents, and osteo-anabolic agents can be provided in the form of kits. Such kits can include the compounds or compositions packaged into dosage units, such as pills or capsules prepared in dispensers or blister packs. If the therapeutic compounds are in liquid form, measuring devices to dispense proper dosage, such as syringes, graduated cylinders, measuring cups, medicine droppers can be included in the kit. The kit may further include additional components useful for proper administration. Exemplary additional components include instructions teaching its methods of use. Formats include compact disc, video, memory cards, and printed medium.

7. EXAMPLES 7.1 Example 1

Effect of Syk inhibitor 2,4-pyrimidinediamine Compound in Preventing Bone Loss in Collagen Induced Bone Degeneration To examine effect of Syk inhibitor 2,4-pyrimidinediamine compound in preventing bone degeneration, a rat collagen induced arthritis model was used (see, e.g., WO 2004/014382, incorporated herein by reference). Rats were immunized with bovine collagen II on day 0 and boosted on day 7. The animals were treated with a vehicle or 2,4-pyrimidinediamine compound 1007 when the animals demonstrated arthritic clinical score of 1 (on days 11-14). Animals were subsequently treated b.i.d. with inhibitor compound or vehicle alone. After 18 days of treatment, hind paw bone structure and integrity were evaluated by X-rays, histopathology, and serum bone marker COMP.

7.2 Example 2

In vitro Effect of Syk Inhibitor Compounds on Osteoclastogenesis and Bone Resorption Detection of osteoclastogenesis. Murine osteoclast precursor cells are cultured in microtitre plates ($1 \times 10^5$/ml, 200 ul/well) in the presence of 30 ng/ml murine CSF-1 and 300 ng/ml RANKL. Test for osteoclastogenesis relies on expression of tartrate resistant alkaline phosphatase (TRAP) enzyme (Shiotani et al., 2002, *Anat. Rec.* 268, 137-146), which is available commercially. TRAP positive multinucleated cells are counted as osteoclast-like multinucleate cells.

Dentin pit formation assay. The in vitro resorption assay for osteoclast activity will employ formation of pits on dentin. In this assay, mouse osteoclast precursors (about $5 \times 10^4$ cells/0.2 ml/well) are placed on dentin slices (4 mm in diameter) in 96-well culture plates and cultured for 1 h with 30 ng/ml M-CSF. Dentin slices are then transferred into 48-well culture plates (Coming Glass). Cells on dentin slices are cultured in the presence of 30 ng/ml M-CSF with or without 200 ng/ml RANKL for 4 days, in the absence or presence of 2,4-pyrimidinediamine compound at about 1 ng/ml to about 20 mg/ml. Culture medium is replaced on day 3. On day 4, cells are removed from the dentin slices with cotton, and the slices are then immersed in Mayer's hematoxylin (Sigma) to stain the resorption pits formed by osteoclasts.

7.3 Example 3

Effect of Syk Inhibitor Compounds on Osteoporosis in Ovariectomized Mice

The effect of Syk inhibitory compounds in limiting bone resorption in animals is tested using ovariectomized mice. An incision is made to the dorsal skin of 8-week old female C57BL/6 mice and the ovaries excised. Sham treated and ovariectomized animals are treated with 0.1 to 100 mg/kg of 2,4-pyrimidinediamine compound at 1 to 3 times a day for up to 4 weeks. Mice are euthanized, and the tibia and femur removed, cleaned of soft tissue, and fixed in 10% formalin. Femurs are scanned by peripheral quantitative computed tomography (pQCT) to examine the total bone density. Alternatively, bone density is measured by dual energy X-ray absorptiometry (e.g., Jilka et al., 1966, *J. Clin. Invest.* 97:1732-1740).

7.4 Example 4

Effect of Syk Inhibitor Compound on Bone Resorption in Gluccocorticoid Treated Mice Glucocorticoid induced osteoporosis will be generated in mice by implanting slow release pellets of placebo or 2.1 mg/km/d of prednisolone for 28 days. This dose of glucocorticosteroid is equivalent to about 20 mg to humans. About 6-11 test animals will be used in each group. Untreated and glucocorticoid treated animals are administered 0.1 to 100 mg/kg of 2,4-pyrimidinediamine compound at 1 to 3 times a day for up to 4 weeks. Spinal bone mass density is measured by DEXA (dual-energy x-ray absorptiometry) determinations or by peripheral quantitative computed tomography (PQCT) to examine the total bone density. For dynamic histomorphometric measurements, tetracycline HCl (30 mg/kg body weight) is given intraperitoneally 6 and 2 d before the mice are killed. For histomorphometry, lumbar vertebrae (L1-L4) are fixed and embedded undecalcified in methyl methacrylate. The histomorphometric examination is done with a computer and digitizer tablet. Trabecular width, trabecular spacing, and wall width are measured directly, whereas the rate of bone formation per cancellous perimeter and activation frequency are calculated (Weinstein et al., 1998, *J. Clin. Invest.* 102:274-282; Weinstein et al., 1997, *Endocrinology* 138:4013-4021).

The foregoing descriptions of specific embodiments have been presented for purposes of illustration and description. They are not intended to be exhaustive or to limit the scope of the disclosure to the precise forms described, and obviously many modifications and variations are possible in light of the above teachings.

All patents, patent applications, publications, and references cited herein are expressly incorporated by reference to the same extent as if each individual publication or patent application was specifically and individually indicated to be incorporated by reference.

What is claimed is:

1. A method of treating a degenerative bone disorder, comprising:
    administering to a subject in need thereof an amount of a Syk inhibitory compound effective to reduce bone loss, wherein the degenerative bone disorder is not associated with an autoimmune disease.

2. The method of claim 1 in which the Syk inhibitory compound is a 2,4-pyrimidinediamine compound.

3. The method of claim 1 in which the degenerative bone disorder is primary osteoporosis.

4. The method of claim 3 in which the primary osteoporosis is selected from the group consisting of postmenopausal osteoporosis, senile osteoporosis, and juvenile osteoporosis.

5. The method of claim 1 in which the degenerative bone disorder is associated with an endocrinopathy.

6. The method of claim 5 in which the endocrinopathy is selected from the group consisting of hypercorticolism, hypogonadism, hyperparathyroidism, and hypoparathyroidism.

7. The method of claim 1 in which the degenerative bone disorder is osteodystrophy.

8. The method of claim 1 in which the degenerative bone disorder is osteopenia.

9. The method of claim 1 in which the degenerative bone disorder is caused by an imbalance of osteoclast and osteoblast activity that results in net excess of bone resorption over bone formation.

10. The method of claim 1 further comprising adjunctively administering an antiresorptive agent.

11. The method of claim 10 in which the antiresorptive agent is selected from the group consisting of bisphosphonates; calcitonin; estrogen and selective estrogen receptor modulators (SERM).

12. The method of claim 1, further comprising adjunctively administering an osteoanabolic agent.

13. The method of claim 12 in which the osteoanabolic agent is selected from the group consisting of parathyroid hormone, strontium renelate, and growth hormone (GH).

14. A method of inhibiting loss of bone, comprising:
    administering to a subject an amount of a Syk inhibitory compound and a bone modulating agent.

15. The method of claim 14 in which the Syk inhibitory compound is a 2,4-pyrimidinediamine compound.

16. The method of claim 14 in which the bone modulating agent is an antiresorptive agent.

17. The method of claim 16 in which the antiresorptive agent is selected from the group consisting of bisphosphonates, calcitonin, estrogen and selective estrogen receptor modulators (SERM).

18. The method of claim 14 in which the bone modulating agent is an osteoanabolic agent.

19. The method of claim 18 in which the osteoanabolic agent is selected from the group consisting of parathyroid hormone, strontium renelate, and growth hormone (GH).

20. The method of claim 14 in which the subject is a menopausal or postmenopausal human female.

21. The method of claim 14 in which the subject is a human female with an estrogen deficiency.

22. The method of claim 14 in which the Syk inhibitory compound impairs the osteoclastogenesis that leads to a net excess of bone resorption over bone formation.

23. A composition comprising:
    a Syk inhibitory compound and a bone modulating agent.

24. The composition of claim 23 in which the Syk inhibitory compound is a 2,4-pyrimidinediamine compound.

25. The composition of claim 23 in which the bone modulating agent is an antiresorptive agent.

26. The composition of claim 25 in which the antiresorptive agent is selected from the group consisting of bisphosphonates, calcitonin, estrogen and selective estrogen receptor modulators (SERM).

27. The composition of claim 23 in which the bone modulating agent is an osteoanabolic agent.

28. The composition of claim 27 in which the osteoanabolic agent is selected from the group consisting of parathyroid hormone, strontium renelate; and growth hormone (GH).

29. The method of claim 10 in which the antiresorptive agent is selected from the group consisting of human calcitonin, salmon calcitonin, rat calcitonin, pig calcitonin, chicken calcitonin, 17β-estradiol, conjugated equine estrogen (CEE), and C-21 progestins.

30. The method of claim 11 wherein the bisphosphonate is alendronate.

31. The composition of claim 26 wherein the bisphosphonate is alendronate.

* * * * *

UNITED STATES PATENT AND TRADEMARK OFFICE
CERTIFICATE OF CORRECTION

PATENT NO. : 7,576,053 B2 Page 1 of 1
APPLICATION NO. : 11/452767
DATED : August 18, 2009
INVENTOR(S) : Masuda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 532 days.

Signed and Sealed this

Seventh Day of September, 2010

David J. Kappos
*Director of the United States Patent and Trademark Office*